(12) United States Patent
Sharon et al.

(10) Patent No.: US 7,659,065 B2
(45) Date of Patent: Feb. 9, 2010

(54) TRANSGENIC FUNGI EXPRESSING BCL-2 AND METHODS OF USING BCL-2 OR PORTIONS THEREOF FOR IMPROVING BIOMASS PRODUCTION, SURVIVAL, LONGEVITY AND STRESS RESISTANCE OF FUNGI

(75) Inventors: Amir Sharon, Karkur (IL); Sima Goldstein-Barhoom, Hod-HaSharon (IL)

(73) Assignee: Ramot At Tel Aviv University Ltd., Tel-Aviv (IL)

(*) Notice: Subject to any disclaimer, the term of this patent is extended or adjusted under 35 U.S.C. 154(b) by 0 days.

(21) Appl. No.: 11/201,322

(22) Filed: Aug. 11, 2005

(65) Prior Publication Data

US 2005/0272129 A1   Dec. 8, 2005

Related U.S. Application Data

(63) Continuation-in-part of application No. PCT/IL2004/000132, filed on Feb. 10, 2004.

(60) Provisional application No. 60/446,513, filed on Feb. 12, 2003.

(51) Int. Cl.
*C12Q 1/68* (2006.01)
*C12P 21/06* (2006.01)
*C12N 15/00* (2006.01)
*C12N 15/82* (2006.01)

(52) U.S. Cl. ............... 435/6; 435/69.1; 435/430; 435/468

(58) Field of Classification Search ............. 435/6, 435/69.1, 430, 468
See application file for complete search history.

(56) References Cited

U.S. PATENT DOCUMENTS

| | | | |
|---|---|---|---|
| 5,266,484 A | 11/1993 | Inoue et al. | |
| 5,814,495 A | 9/1998 | Della-Cioppa et al. | |
| 5,866,380 A | 2/1999 | Lesage-Meessen et al. | |
| 5,877,014 A | 3/1999 | Shetty et al. | |
| 5,945,328 A | 8/1999 | Woldike et al. | |
| 6,004,785 A * | 12/1999 | Berka et al. | 435/484 |
| 6,015,687 A | 1/2000 | Kiefer et al. | |
| 6,017,870 A | 1/2000 | Bower et al. | |
| 6,080,567 A | 6/2000 | Kofod et al. | |
| 6,090,574 A | 7/2000 | Giuseppin et al. | |
| 6,103,490 A | 8/2000 | Berka et al. | |
| 6,130,063 A | 10/2000 | Lawlis | |
| 6,156,553 A | 12/2000 | Christensen et al. | |
| 6,171,817 B1 | 1/2001 | Berka et al. | |
| 6,221,335 B1 | 4/2001 | Foster | |
| 6,255,115 B1 | 7/2001 | Beijersbergen et al. | |
| 6,310,272 B1 | 10/2001 | Ohashi et al. | |
| 6,350,602 B1 | 2/2002 | Van Gorcom et al. | |
| 6,365,410 B1 | 4/2002 | Schellenberger et al. | |
| 6,403,362 B1 | 6/2002 | Moriya et al. | |
| 6,432,672 B1 | 8/2002 | Selten et al. | |
| 6,436,393 B1 | 8/2002 | Bilbao et al. | |
| 6,475,772 B1 | 11/2002 | Kalra et al. | |
| 2005/0272129 A1 | 12/2005 | Sharon et al. | |

FOREIGN PATENT DOCUMENTS

| | | |
|---|---|---|
| EP | 00137280 | 3/1992 |
| EP | 0215594 | 1/1995 |
| WO | WO 01/18219 | 3/2001 |
| WO | WO 02/055684 | 7/2002 |
| WO | WO 2004/072225 | 8/2004 |

OTHER PUBLICATIONS

Longo et al., Human Bcl-2 reverses survival defects in yeast lacking superoxide dismutase and delays death of wild-type yeast. J Cell Biol. Jun. 30, 1997;137(7):1581-8.*
Robinson et al., Transformation of the bioherbicide Colletotrichum gloeosporioides f. sp. Aeschynomene By electroporation of germinated conidia. Curr Genet. Aug. 1999;36(1-2):98-104.*
Punt et al., Tranformation of Aspergillus based on the hygromycin B resistance marker from *Escherichia coli*. Gene. 1987;56(1):117-24.*
http:// www.tolweb.org/Ascomycota.*
Gouka et al., Efficient production of secreted proteins by *Aspergillus*: progress, limitations and prospects. Appl Microbiol Biotechnol. Jan. 1997;47(1):1-11.*
Watson et al., Recombinant DNA, Second Edition, 2nd ed. Distributed by W. H. Freeman and Company, 2001. pp. 51-52; 153-155.*
Bowman et al.,Molecular evolution of the fungi: Relationship of the Basidiomycetes, Ascomycetes and Chytridiomycetes 1992, Mol. Biol. Evol. 285-296.*
Ascomycota, Tree of Life, http://tolweb.org/tree, pp. 1-8.*
Coultas et al., Bfk: a novel weakly proapoptotic member of the Bcl-2 protein family with a BH3 and a BH2 region. Cell Death Differ. Feb. 2003;10(2):185-92.*

(Continued)

*Primary Examiner*—Maria Leavitt

(57) ABSTRACT

Methods for enhancing growth in fungi and, more particularly, transgenic fungi expressing the Bcl-2 gene having improved biomass production, survival, longevity and stress resistance in solid and liquid culture are disclosed. Also disclosed are methods of using the transgenic fungi of the present invention for biocontrol.

Figure 1A:
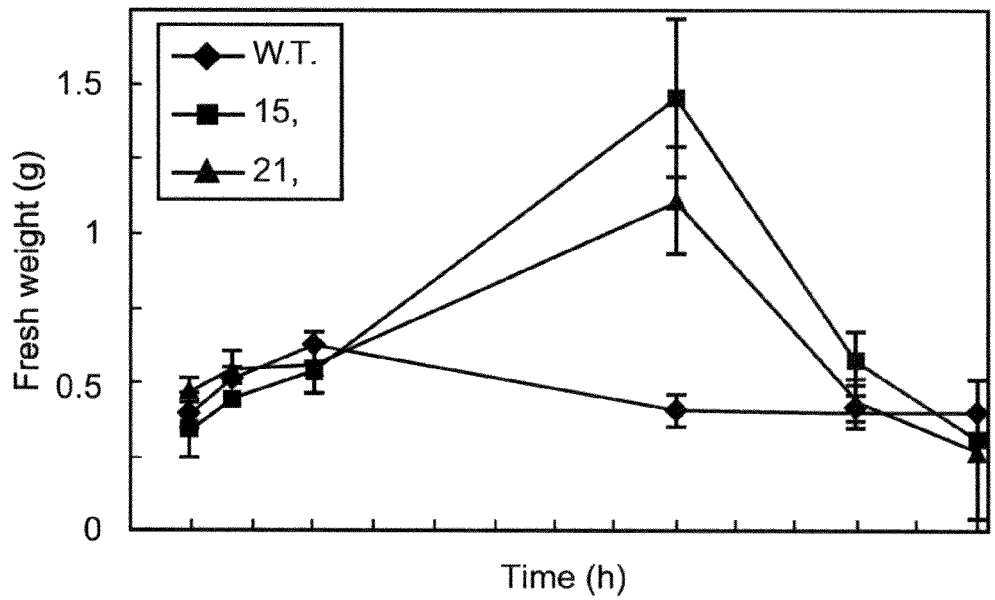

12 Claims, 10 Drawing Sheets
(5 of 10 Drawing Sheet(s) Filed in Color)

OTHER PUBLICATIONS

Jang et al., Bcl-2 attenuation of oxidative cell death is associated with up-regulation of gamma-glutamylcysteine ligase via constitutive NF-kappaB activation. J Biol Chem. Sep. 10, 2004;279(37):38779-86. Epub Jun. 18, 2004.*

Lutz R. J. Role of the BH3 (Bcl-2 homology 3) domain in the regulation of apoptosis and Bcl-2-related proteins. Biochem. Soc. Trans. (2000) 28, (51-56).*

Voet et al., Biochemistry John Wiley and Sons, 1990, p. 126-128.*

Kimchi-Sarfaty Cet al., A "silent" polymorphism in the MDR1 gene changes substrate specificity.Science. Jan. 26, 2007;315(5811):525-8.*

Y Tsujimoto et al., Analysis of the structure, transcripts, and protein products of bcl-2, the gene involved in human follicular lymphoma Proc. Natl. Acad. Sci. U.S.A. 83 (14), 5214-5218 (1986).*

Reed "Bcl-2 Family Proteins", Oncogene, 17(25): 3225-3236, 1998.

Tsujimoto et al. "Analysis of the Structure, Transcripts and Protein Products of Bcl-2, the Gene Involved in Human Follicular Lymphoma", Proceedings of the National Academy of Science, USA, 83: 5214-5218, 1986.

Gross et al. "Biochemical and Genetic Analysis of the Mitochondrial Response of Yeast to BAX and BCL-XL", Mocular and Cellular Biology, 20(9): 3125-3136, 2000.

Hynes et al. "Isolation of Genomic Clones Containing the AmdS Gene of *Aspergillus nidulans* and Their Use in the Analysis of Structural and Regulatory Mutations", Molecular and Cellular Biology, 3(8): 1430-1439, 1983.

Innis et al. "Expression, Glycosylation, and Secretion of An *Aspergillus glucoamylase* by Saccaromyces Cerevisiae", Science, 228:21-27, 1985.

Johnstone et al. "Cloning An *Aspergillus nidulans* Developmental Gene by Transformation", The EMBO Journal, 4(5): 1307-1311, 1985.

Kelly et al. "Transformation of *Aspergillus niger* by the AmdS Gene of *Aspergillus nidulans*", The EMBO Journal, 4(2): 475-479, 1985.

Kinsey et al. "Transformation of Neurospora Crassa With the Cloned Am (*Glutamate dehydrogenase*) Gene", Molecular and Cellular Biology, 4(1): 117-122, 1984.

Lee et al. "FluG and FlbA Function Interdependently to Initiate Conidiophore Development in *Aspergillus nidulans* Through BrlAβ Activation", The EMBO Journal, 15(2): 299-309, 1995.

St. Leger et al. "Construction of An Improved Mycoinsecticide Overexpressing A Toxic Protease", Proc. Natl. Acad. Sci. USA, 93: 6349-6354, 1996.

Lockington et al. "Cloning and Characterization of the Ethanol Utilization Regulon in *Aspergillus nidulans*", Gene: 33(2):137-149, 1985. Abstract.

McKnight et al. "Nucleotide Sequence of the *Triosephosphate isomerase* Gene From *Aspergillus nidulans*: Implications for A Differential Loss of Introns", Cell, 46(1): 143-147, 1986. Abstract.

Mitsuhara et al. "Animal Cell-Death Suppressors Bcl-XL and Ced-9 Inhibit Cell Death in Tobacco Plants", Current Biology, 9: 775-778, 1999.

Mullaney et al. "Primary Structure of the TrpC Gene From *Aspergillus nidulans*", Molecular Genetics and Genomics, 199(1): 37-45, 1985. Abstract.

Nunberg et al. "Molecular Cloning and Characterization of the Glucoamylase Gene of *Aspergillus awamori*", Molecular and Cellular Biology, 4(11): 2306-2315, 1984.

Reed "Double Identity for Proteins of the Bcl-2 Family", Nature, 387: 773-776, 1997.

Ruijter et al. "Production of Organic Acids by Fungi", The Mycota, X: 213-230, 2002. Abstract.

Schmidt "Beta-Lactam Antibiotics: Aspects of Manifacture and Therapy",The Mycota, X: 69-91, 2002. Abstract.

Sewell et al. "AbaA Controls Phialide Differentiation in *Aspergiilus nidulans*", The Plant Cell, 2: 731-739, 1990.

Shangary et al. "Peptides Derived From BH3 Domains of Bcl-2 Family Members: A Comparative Analysis of Inhibition of Bcl-2, Bcl-XL and Bax Oligomerization, Induction of Cytochrome C Release, and Activation of Cell Death", Biochemistry, 41: 9485-9495, 2002.

Simpson et al. "Mutants With General Growth Rate Advantages Are the Predominant Morphological Mutants to Be Isolated From the Quorn® Production Plant", Mycological Research, 102(2): 221-227, 1998.

Stohl et al. "Construction of A Shuttle Vector for the Filamentous Fungus *Neurospora crassa*", Proc. Natl. Acad. Sci. USA, 80: 1058-1062, 1983.

Tilburn et al. "Transformation by Integration in *Aspergillus nidulans*", Gene, 26(2-3): 205-221, 1983. Abstract.

Turgeon Application of Mating Type Gene Technology to Problems in Fungal Biology; Annual Reviews in Phytopathology, 36: 115-137, 1998.

Wiebe et al. "Use of A Series of Chemostat Cultures to Isolate 'Improved' Variants of the Quorn Mycoprotien Fungus, *Fusarium graminearum* A3/5", Microbiology, 140: 3015-3021, 1994. Abstract.

Williams et al. "Introduction of Foreign Genes Into Tissues of Living Mice by DNA-Coated Microprojectiles", Proc. Natl. Acad. Sci. USA, 88: 2726-2730, 1991.

Yamada et al. "Cloning and Functional analysis of the *Aspergillus oryzae* Conidiation Regulator Gene BrlA by Its Disruption and Misscheduled Expression", Journal of Bioscience and Bioengineering, 87(4): 424-429, 1999.

Yelton et al. Transformation of *Aspergillus nidulans* by Using A TrpC Plasmid,. Proc. Natl. Acad. Sci. USA, 81: 1470-1474, 1984.

Zamzami et al. "Subcellular and Submitochondrial Mode of Action of BcI-2-Like Oncoproteins", Oncogene, 16: 2265-2282, 1998.

Zhang et al. "*Drosophila* Pro-Apoptotic Bcl-2/Bax Homologue Revelas Evolutionary Conservation of Cell Death Mechanisms", The Journal of Biological Chemistry, 275(35): 27303-27306, 2000.

Tsujimoto et al. "Human B-Cell Leukemia/Lymphoma 2 (BCL-2) Proto-Oncogene mRNA Encoding BCL-2-Beta Protein, Complete Cds", Database EMBL, 1994.

Gross et al. "BCL-2 Family Members and the Mitochondria in Apoptosis", Genes and Development, 13(15): 1899-1911, 1999.

Kane et al. "BCL-2 Inhibition of Neural Death: Decreased Generation of Reactive Oxygen Species", Science, 262(5137): 1274-1277, 1993.

Xu et al. "Methods of Assaying BCL-2 and BAX Family Proteins in Yeast", Methods: A Companion to Methods in Enzymology, 17(4): 292-304, 1999.

Tao et al. "Modulation of Cell Death in Yeast by the BCL-2 Family of Proteins", Journal of Biological Chemistry, 272(24): 15547-15552, 1997.

Acsadi et al. "Human Dystrophin Expression in MDX Mice After Intramuscular Injection of DNA Constructs", Nature, 352(6338): 815-818, 1991.

Alnemri et al. "Overexpressed Full-Length Human BCL2 Extends the Survival of Baculovirus-Infected Sf9 Insect Cells", Proc. Natl. Acad. Sci. USA, 89: 7295-7299, 1992.

Amsellem et al. "Engineering Hypervirulence in A Mycoherbicidal Fungus for Efficient Weed Control", Nature Biotechnology, 20: 1035-1039, 2002.

Esser et al. "The Mycota. A Comprehensive Treatise on Fungi as Experimental Systems for Basic and Applied Research. X. Industrial Applications", Microbiology Today: Book Reviews, Society for General Microbiology, 2002. Abstract.

Balance et al. "Transformation of *Aspergillus nidulans* by the Orotidine-5'-Phosphate Decarboxylase Gene of *Neurospora crassa*", Biochemical & Biophysical Research Communications, 112(1): 284-289, 1983. Abstract.

Barclay et al. "Efficient Transformation of Dictyostelium Discoideum Amoebae", Molecular and Cellular Biology, 3(12): 2117-2130, 1983.

Barhoom et al. "cAMP Regulation of 'Pathogenic' and 'Saprophytic' Fungal Spore Germination", Fungal Genetics and Biology, 41: 317-326, 2004.

Boel et al. "Two Different Types of Intervening Sequences in the *Glucoamylase* Gene From *Aspergillus niger*", The EMBO Journal, 3(7): 1581-1585, 1984.

Borner "The BcI-2 Protein Family: Sensors and Checkpoints for Life-or-Death Decisions", Molecular Immunology, 39: 615-647, 2003.

Bull et al. "Heavily Methylated Amplified DNA in Transforma of *Neurospora crassa*", Nature, 310: 701-704, 1984. Abstract.

Bussink et al. "Identification of Two Highly Divergent Catalase Genes in the Fungal Tomato Pathogen, *Cladosporium fulvum*", European Journal of Biochemistry, 268: 15-24, 2001.

Case et al. "Efficient Transformation of *Neurospora crassa* by Utilizing Hybrid Plasmid DNA", Proc. Natl. Acad. Sci. USA, 76(10): 5259-5263, 1979.

Chang et al. "Directed Replacement of Mt A by Mt A-1 Effects A Mating Type Switch in *Neurospora crassa*", Genetics, 138: 75-81, 1994.

Chou et al. "Solution Structure of BID, An Intracellular Amplifier of Apoptotic Signaling", Cell, 96: 615-624, 1999.

Derossi et al. "Cell Internalization of the Third Helix of the Antennapedia Homeodomain Is Receptor-Independent", The Journal of Biological Chemistry, 271(30)18188-18193, 1996.

Dickman et al. "Abrogation of Disease Development in Plants Expressing Animal *Antiapoptotic genes*", Proc. Natl. Acad. Sci. USA, 98(12): 6957-6962, 2001.

Dubensky et al. "Direct Transfection of Viral and Plasmid DNA Into the Liver or Spleen of Mice", Proc. Natl. Acad. Sci. USA, 81: 7529-7533, 1984.

Goodwin et al. "A Catalase Gene of Colletotrichum Gloeosporioides f. Sp. Malvae Is Highly Expressed During the Necrotrophic Phase of Infection of Round-Leaved Mallow, Malva Pusilla", FEMS Microbiology Letters, 202: 103-107, 2001.

Fang et al. "The SOD2 Gene, Encoding A manganese-Type Superoxide Dismutase, Is Up-Regulated During Conidiogenesis in the Plant-Pathogenic Fungus Colletotrichum Graminicola", Fungal Genetics and Biology, 36: 155-165, 2002.

Lau et al. "Acropetal: A Genetic Locus Rquired for Conidiophore Architecture and Pathogenicity in the Rice Blast Fungus", Fungal Genetics and Biology, 24: 228-239, 1998.

Futami et al. "Optimum Modification for the Highest Cytotoxicity of Cationized Ribonuclease", Journal of Biochemistry, 132: 223-228, 2002.

Grant et al. "Transformation of *Neurospora crassa* With Recombinant Plasmids Containing the Cloned Glutamate Dehydrogenase (Am) Gene: Evidence for Autonomous Replication of the Transforming Plasmid", Molecular and Cellular Biology, 4(10): 2041-2051, 1984.

Gressel "Enhancing Microbiocontrol of Weeds. Future Biocontrol Preparations Will Likely Carry Specific Hypervirulence and Other Genes to Keep the Agents on Target, Overcome Host Defenses", ASM News, 69(10): 498-502, 2003.

Gressel "Potential Failsafe Mechanisms Against the Spread and Introgression of Transgenic Hypervirulent Biocontrol Fungi", Trends in Biotechnology, 19(4): 149-154, 2001.

International Search Report and Written Opinion Dated Aug. 12, 2004 From the International Searching Authority Re.: Application No. PCT/IL2004/000132.

Official Action Dated Mar. 2, 2006 From the US Patent Office Re.: U.S. Appl. No. 11/201,322.

Official Action Dated Apr. 9, 2008 From the US Patent Office Re.: U.S. Appl. No. 11/201,322.

Official Action Dated Jun. 19, 2006 From the US Patent Office Re.: U.S. Appl. No. 11/201,322.

Official Action Dated May 20, 2008 From the US Patent Office Re.: U.S. Appl. No. 11/201,322.

Official Action Dated Jul. 24, 2007 From the US Patent Office Re.: U.S. Appl. No. 11/201,322.

Official Action Dated Sep. 24, 2008 From the US Patent Office Re.: U.S. Appl. No. 11/201,322.

Official Action Dated Nov. 30, 2006 From the US Patent Office Re.: U.S. Appl. No. 11/201,322.

Bowman et al. "Molecular Evolution of the fungi: Relationship of the Basidiomycetes, Ascomycetes, and Chytridiomycetes", Molecular Biology Evolution, 9(2): 285-296, 1992.

Coultas et al. "Bfk: A Novel Weakly Proapoptotic Member of the Bcl-2 Protein Family With A BH3 and A BH2 Region", Cell Death and Differentiation, 10(2):185-192, 2003.

Gouka et al. "Efficient Production of Secreted Proteins by *Aspergillus*: Progress, Limitations and Prospects", Applied Microbiology & Biotechnology, 47: 1-11, 1997.

Jang et al. "Bcl-2 Attenuation of Oxidative Cell Death Is Associated With Up-Regulation of γ-Glutamylcysteine Ligase Via Constitutive NF-κB Activation", The Journal of Biological Chemistry, 279(37): 38779-38786, Sep. 10, 2004.

Kimchi-Sarfaty et al. "A 'Silent' Polymorphism in the MDR1 Gene Changes Substrate Specificity", Science, 315(5811): 525-528, Erratum, Jan. 26, 2007.

Longo et al. "Human Bcl-2 Reverses Survival Defects in Yeast Lacking Superoxide Dismutase and Delays Death of Wild-Type Yeast", The Journal of Cell Biology, 137(7): 1581-1588, 1997.

Lutz "Role of the BH3 (Bcl-2 Homology 3) Domain in the Regulation of *Apoptosis* and Bcl-2-Related Proteins", Biochemical Society Transactions, 28(Pt.2): 51-56, 2000.

Punt et al. "Transformation of *Aspergillus* Based on the Hygromycin B Restistance Marker From *Escherichia coli*", Gene, 56: 117-124, 1987.

Robinson et al. "Transformation of the Bioherbicide Colletotrichum Gloeosporioides F. Sp. Aeschynomene by Electroporation of Germinated Conidia", Current Genetics, 36: 98-104, 1999.

Taylor et al. "Ascomycota. Sac Fungi", The Tree of Life, Web Project, http://tolweb.org/tree, P.1-8, 1996.

Voet et al. "Chemical Evolution", Biochemistry, Chap.6(Sec.6-3): 126-128, 1990.

Watson et al. "The Genetic Elements That Control Gene Expression/ Controlling Eukaryotic Gene Expression", Recombinant DNA, 2nd Ed., Chap.4/9: 51-52, 153-155, 2001.

\* cited by examiner

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 1
gcatagatct ttcacttgtg gccc                                            24

<210> SEQ ID NO 2
<211> LENGTH: 30
<212> TYPE: DNA
<213> ORGANISM: Artificial sequence
<220> FEATURE:
```

<223> OTHER INFORMATION: Single strand DNA oligonucleotide

<400> SEQUENCE: 2
ggaaccatgg cgcacgctgg gagaacgggc                                              30

<210> SEQ ID NO 3
<211> LENGTH: 180
<212> TYPE: DNA
<213> ORGANISM: Colletotrichum gloeosporioides

<400> SEQUENCE: 3
cgcatgggtg agttttatat gtcaattctg gtatgtgctt tgtctaacat atattaggtc      60
ctacctttgg cgccatggct ctctcgggtg tcaaggccgc cgaggaggct ctcaagatct     120
tcgacactcg caagaagcag aacgatctgc aagcgagatc atcaaagaag gtcatagttg     180

<210> SEQ ID NO 4
<211> LENGTH: 856
<212> TYPE: DNA
<213> ORGANISM: Colletotrichum gloeosporioides

<400> SEQUENCE: 4
tagctctaat acgactcact atagggaaag cttgcatgca ggcctctgca gtcgacgggc      60
ccgggatccg attggcggtg gcggtgggtg tccgggtaag agaagagacg ccctggagg      120
acggggtcgg cagagggctc aacgccggga accaggtgag agggagagaa ggcgacctgc     180
tcaatctcgg cgaagtagtt ctcggggttc ttgttgaggg tgagcttgcc gaagggcctc     240
aaggggacct cgctctgagg ccagaccttt gtcaggtcaa agacgttcca tttgaatttc     300
tcagcctgct cgggggtaag agtctgaacg tagacggtcc agctggggtg gtcgcccttc     360
tggatagact cgaacaggtc ctgggtgtgc cagtcagggt tctcggacgc catcttgcca     420
gcctcctcgt tggtaaaagt cttgtttcct tggtcggtct tcaagtgaat ctggacgtaa     480
acgaaagagc catcgggctt ggtccacttg tgcgtgtgtc cggataaacc gttcatgtgt     540
ctgtaggagt aaggagttcc gcgatcagag aacaaatgca tcaattgatg gacgcattca     600
gggtgatttc cgccagtaat cgaactagat ttaacgttaa aaagcgttat ttcaagtcca     660
gaaatcaatt gcttacattc tggctgagtt agcaaagtcg tgatgcgagt tgggtgttga     720
actccatggg tggcatcctt caggttatttt gcgggttggc gctttggtgg aatgaaacct     780
aaaaccggta aaacgcccga tgacaatctt catttcaatt accggaaaaa aaccggcccg     840
aaggaaaaaa atggat                                                   856

<210> SEQ ID NO 5
<211> LENGTH: 767
<212> TYPE: DNA
<213> ORGANISM: Colletotrichum gloeosporioides

<400> SEQUENCE: 5
cagctctaat acgactcact atagggaaag cttgcatgca ggcctctgca gtcgacgggc      60
ccgggatccg attggtagta cgcgtgctcc cacatgtcga caccgaagac gggcacgccc     120
ttggtgacgg ggtcctggtc cttggtcgtg atgatgctga acctgttgt gtcgtccttg     180
accagccaac cccagccgct gccggtgatg cccaacagcg cagcgttgaa tgcttgcttg     240
aacttgtcca ggctgcccca gacacgggta atctcggcga tcaggctggg tgcggagtcg     300
ggagaagcat ccgggctaga ggcggggaa aggttctccc agaagaggga gtggttgatg     360
tggcctccac cgtgaaagtt gagtgccgcc aaaacggcga tgcggctttg gagagggttg     420

-continued

```
gcgttgtatg tttcgatggc cttgtttagg tttgtgacgt acgtctggtg gtgcttgctg    480
tggtgaagct catgatttgg gccgagatgt gcggttccaa tgccttcgga ggggttagcc    540
agagttctgg tgccgaagca ggggtgatac atacgtctac acatatggga accttagcaa    600
taatctaatg cattcgccga ggtaccgagc ctcgaattaa ctggcctcgt tttacaactt    660
cgtgactgag gaaaatccct tggccttact ccaacttaat accctggtac atcccctttt    720
gccagacctg ggcgtaataa ccaaaaggcc cccccacgat cgcctttt                  767
```

TRANSGENIC FUNGI EXPRESSING BCL-2 AND METHODS OF USING BCL-2 OR PORTIONS THEREOF FOR IMPROVING BIOMASS PRODUCTION, SURVIVAL, LONGEVITY AND STRESS RESISTANCE OF FUNGI

RELATED APPLICATIONS

The present application is a Continuation-In-Part (CIP) of PCT Application No. PCT/IL2004/000132, filed on Feb. 10, 2004, which claims priority from U.S. Provisional Patent Application No. 60/446,513, filed on Feb. 12, 2003, the contents of which are incorporated herein by reference.

FIELD AND BACKGROUND OF THE INVENTION

The present invention relates to a method for enhancing growth in fungi and, more particularly, to the use of Bcl-2 or portions thereof for improving biomass production, survival, longevity, stress resistance and pathogenicity of filamentous fungi grown in solid or liquid culture.

Filamentous Fungus

From economic point of view, fungi dominate biotechnology. They are used in a variety of major industrial processes such as food and drug production, industrial paper and pulp production, agriculture, bioremediation and others. Perhaps the most well known metabolites produced by fungi are the β-lactam antibiotics produced by *Penicillium, Acremonium,* and *Aspergillus* species. Despite their availability for over 50 years, β-lactams still command 50% of the world market for systemic antibiotics which, in 1998 totaled nearly 21.5 billion US dollars, making it one of the most important categories of pharmaceutical sales (Schmidt, F. R. In: Esser, K. and Bennett, J. W. eds. The Mycota. 2002; Vol X, H. D. Osiewacz ed. Industrial Applications. Springer, Berlin, pp. 69-92). Of these, the total sales volume (1998) of cephalosporins was about 7 billion US dollars and that of broad-spectrum penicillins nearly 4 billion dollars. Improved strains have been generated that produce up to 50 g/liter penicillin and up to 30 g/liter cephalosporin, representing 50,000 fold improvement compared to production rates of the original strains. For many years, however, no further improvements in antibiotic production (β-lactams and non-β-lactams) rates have been achieved, mostly due to bottlenecks related to fermentation performance.

Another important group of therapeutic compounds are immunosuppressants (Anke T. ed. 1997; Fungal Biotechnology. Chapman and Hall, London; Kurnsteiner, H. et al. In: Esser, K. and Bennett, J. W. eds. The Mycota. 2002 Vol X, H. D. Osiewacz ed. Industrial Applications. Springer, Berlin, pp. 129-156). The most widely used compound in this category is cyclosporin A from *Tolypocladium* sp. with annual sales of approximately 2 billion US dollars. Similar to other fungal metabolites, cyclosporin A is produced mainly in submerged fermentation, and improvements in production performance are greatly needed.

Organic acids are another category of compounds that are widely produced by fungi. Citric acid is by far the most important organic acid in production volume (900,000 tons in 2000) as well as knowledge available (Ruijter, G. J. G. et al. In: Esser, K. and Bennett, J. W. eds. The Mycota. 2002, Vol X, H. D. Osiewacz ed. Industrial Applications. Springer, Berlin, pp. 213-230). Citric acid is mostly produced in submerged fermentation by the fungus *A. niger*. It is the most widely used organic acid in foods, beverages, pharmaceuticals, and technical applications. A number of other organic acids are produced by *A. niger* and other *Aspergillus* species, including fumaric acid, lactic acid, and gluconic acid. A range of additional secondary metabolites is produce in fermentation by fungi including vitamins, flavors, carotenoids, gibberellic acid, and more (for reviews see Oseiwacz, H. D. ed. In Esser, K. and Bennett, J. W. eds. The Mycota, 2002, Vol X, Springer, Berlin).

Fungal enzymes are crucial to various processes of the food and paper industries, as well as for bioremediation (waste treatment). Examples are the industrially produced cell wall degrading enzymes such as the cellulases, pectinases and xylanases. These enzymes are used mainly in fruit juice clarification, enzymatic pulping, in the baking industry, for paper bleaching and as animal feed. Edible fungal products are yet another large market. In addition to edible mushrooms, fungi are used in the food industry e.g., in cheese (*Penicillium roqueforti, P. camemberti*) and tofu production, production of flavorings, and as a protein source. Quorn, a mycoprotein produced in fermentation by *Fusarium venenatum* (syn *graminearum*) strain A3/5 has an annual sales volume of 200 million US dollars. Thus, there is a constant demand for *F. venenatum* A3/5 strains having improved growth rate and better performance in liquid fermentation (Wiebe, M. G. et al. Microbiology 1994;140: 3015-3021; Simpson, D. R., et al. Mycol Res 1998;102: 221-227).

Another area where fungi are widely used is for biological control of agricultural pests. Fungal biopesticides include bionematocides, bioinsecticides, biofungicides and bioherbicides. Most biological control products use fungal spores as the active ingredient. However, efficient pest control almost always involves application of large quantities of the biopesticide, which, in turn requires extremely large numbers of spores. For example, effective weed control with the leading bioherbicide product Collego requires $10^{12}$ spores per acre (Watson, A. K., et al. In: Prusky, D., Freeman, S. and Dickman, B. M. eds. *Colletotrichum*: Host Specificity, Pathology and Host-Pathogen Interaction. 2000; APS Press, St. Paul, Minn.). Furthermore, fungal fermentation products are often temperature sensitive and need to be stored under carefully controlled conditions, making the efficiency of spore production in solid or liquid fermentations, and spore quality important constituents of the cost of these products.

The abovementioned examples demonstrate the great economical importance, and yet unexploited potential of fungi. Of the bottlenecks in many fermentation processes, biomass production and sustainability of the culture during fermentation are crucial. Therefore, enhancement of growth rate, extenuation of the vegetative growth phase in culture, enhanced spore production, and improved resistance to environmental stress etc., all are highly desired traits that have wide applications in better utilization of fungi.

Bcl-2

Bcl-2 is a member of a superfamily of genes important to the regulation of programmed cell death processes known as apoptosis. The apoptotic-suppressing Bcl-2 gene was discovered as a proto-oncogene found at the breakpoints of the T(14/18) chromosomal translocations in low-grade B-cell lymphomas (Gross, A., et al. Genes and Development 1999; 13: 1899-1911). Members of the Bcl-2 superfamily possess up to four-conserved Bcl-2 homology (BH) domains designated BH1, BH2, BH3 and BH4, which correspond to α-helical segments (Reed, C. J. Oncogene 1998;17: 3225-3236). Pro apoptotic genes contain only 3 BH domains while anti-apoptotic genes contain all four BH domains. Deletion and mutagenesis studies revealed that the BH3 domain, and the presence of an alpha-helical transmembrane domain at the N-terminus are critical in the pro-apoptotic members for both dimerization with the anti-apoptotic proteins and for induction of apoptosis (Chou, J. J. et al. Cell 1999;96: 615-624). Examples of genes belonging to the Bcl-2 superfamily include the mammalian bcl-2, bax, bcl-$X_L$, bcl-xS, bad, bak, A1 and Mcl-1 genes, CED-9 from *C. elegans*, the BHRF1 gene (derived from Epstein-Barr virus) and the LMW5-HL gene (derived from African Swine Fever virus) (Takayama et al. Experimental Medicine, 1995;13: 24-31).

At least three general functions for Bcl-2 and some of its anti-apoptotic homologues such as Bcl-$X_L$ have been identified: (a) dimerization with other Bcl-2 family members; (b) Binding to non-homologous signal proteins involved in signal transduction, such as the protein kinase Raf-1, the protein phosphatase calcineurin and the small GTPases R-Ras and H-Ras; and (c) Formation of ion-channels pores (Reed, C. J. Oncogene 1998;17: 3225-3236; Reed, C. J. Nature 1997a; 387: 773-776; Zamzami, N. et al. Oncogene 1998a; 16: 2265-2282). Several biological effects of Bcl-2 on intact cells have been observed: Bcl-2 might act on plasma membrane (prevention of phosphatidylserine activity), on the cellular redox potential (decrease in lipid peroxidation, inhibition of reactive oxygen species, increase in catalase and superoxide dismutase, elevated NAD-/NADH ratio), effects on proteases (inhibition of caspase 3 and 6). Other effects of Bcl-2 include effects on intracellular ions (prevention of cytoplasmic acidification, inhibition of $Ca^{++}$ uptake into the nucleus and ER) and effects on mitochondria (inhibition of pre-apoptotic mitochondrial transmembrane potential disruption, prevention of $Ca^{++}$ influx, prevention of cytochrome C outflow from the intermembrane space, etc.). One of the first common manifestations of the apoptotic process, irrespective of the cell type and the induction stimulus, is a disruption of the mitochondrial membrane function that marks the "point of no return" of the apoptotic process. Given the functional importance of the Bcl-2 gene and it's homologues in apoptosis control, the Bcl-2 superfamily constitute prime targets for therapeutic interventions on numerous disease states. For example, it has been proposed that agents based on the proapoptotic Bax and Bad BH3 domains may have therapeutic value in induction of apoptosis in certain cancers (Shangary, S. and Johnson, D. E, Biochemistry 2002, 41; 9485-95).

Generally, it is known in the art that overall identity and homology among the genes belonging to the Bcl-2 superfamily, and having similar function, is surprisingly low at the nucleic acid and amino acid sequence levels. For example, identity between Baxa and Bcl-2 is about 21% and similarity there between is about 43% at their amino acid sequence level (Yamamoto, "Intercellular Signal Transduction", Experimental Medicine, supp., Adduce Co., Ltd.). Nonetheless, the ability of Bcl-2 superfamily proteins to regulate cell life and death is conserved across evolution. For example, the nematode *Caenorhabditis elegans* contains a Bcl-2 homologue, CED-9, that is essential for the viability of these animals: thus, expression of the human Bcl-2 protein in *C. elegans* can rescue ced-9-deficient worms (Vaux et al., 1992; Hengartner and Horvitz, 1994). The human Bcl-2 protein can also block apoptotic cell death in insect cells (Alnemri, E. S. et al. Proc. Natl. Acad. Sci. USA 1992;89: 7295-7299), and can protect some yeast mutants from death induced by oxidative injury (Kane, D. J. et al. Science 1993;262: 1274-1276). Similarly, cell death induced by UV-B irradiation was suppressed in transgenic plants expressing Bcl-$X_L$ (Mitsuhara, I. et al. Current Biology 1999;9: 775-778). This is most likely due to the high interspecies sequence homology of the anti- and pro-apoptotic BH domains, with BH1 and BH2 being anti-apoptotic in character, and BH3 clearly associated with induction of apoptosis (Zhang et al, J Bio Chem 2000; 275:27303-06).

Application of the potential benefits of enhanced vigor, longevity and stress resistance conferred by expression of anti-apoptotic genes of the Bcl-2 family, such as Bcl-2, Bcl-$X_L$ and CED-9 has been proposed for a variety of organisms. For example, Bilbao et al. (U.S. Pat. No. 6,436,393) disclose adenovirus vectors encoding human Bcl-2 for transformation and protection of mammalian cells and organs during cryopreservation and transplantation. Expression of the Bcl-2 gene, under control of the CMV promoter, in transformed cells or transgenic animals, led to enhanced resistance to both freezing and thawing stress. In another application, human Bcl-$X_L$ and nematode CED-9 genes were introduced into tobacco plants by *Agrobacterium* transformation (U.S. Pat. No. 6,310,272 to Ohasi et al.), producing transgenic tobacco plants exhibiting enhanced resistance to UV, superoxide and salt stress. Similarly, Dickman, et al. (Dickman et al. PNAS USA 2001, 98: 6957-62), also using *Agrobacterium* transformation, generated transgenic tobacco plants expressing the human Bcl-2, Bcl-$X_L$, nematode CED-9 and baculovirus op-iap members of the Bcl-2 family, all of which demonstrated heritable resistance to several necrotrophic fungal phytopathogens and tomato spotted wilt virus. Transformation of filamentous fingi with genes of the Bcl-2 family has not been reported.

Genetic Manipulation in Fungi

Traditionally, industrially important fungal species, such as the abovementioned *Penicillium, Fusarium, Tolypocladium, Trichoderma*, and *Aspergillus* sp., have been subjected to ongoing selection in the interest of optimizing production of desired metabolites or metabolic processes. For example, Inoue et al. reported the isolation of a fungus "overproducing" Streptovaricin C (U.S. Pat. No. 5,266,484 to Inoue et al.). Similarly, efforts have been undertaken for direction of fungal evolution, and favor the appearance of desired traits: for example, Kaira et al. (U.S. Pat. No. 6,475,772) and Scheilenberger et al. (U.S. Pat. No. 6,365,410) combined manipulation of rate of mutagenesis with careful choice of selection conditions to enhance production of fermentation products such as biofungicides. However, such selection methods are complex, laborious and costly, and with often unpredictable results.

Transformation and expression in filamentous fungi involving homologous expression has also been reported. Examples of homologous expression in filamentous fungi include the complementation of *N. crassa* mutants lacking key biosynthetic pathways, the complementation of the auxotrophic markers trpC, and argB in *A. nidulans* and the transformation of *A. nidulans* to acetamide or acrylamide utilization by expression of the *A. nidulans* gene encoding acetamidase (see, for example, Stohl et al. PNAS USA 1983; 80:1058-62 or Grant et al. Mol Cell Bio 1984;4:2041-51; for an exhaustive review of homologous transformation see Hynes, M J Exper Mycology 1986; 10:1-8). Beijeresbergen et al. (U.S. Pat. No. 6,255,115) disclose the transformation of filamentous fungi such as *A. awamori* with homologous genes (from *Fusarium*) using the *Agrobacterium tumifaciens* Ti plasmid, affording a method of producing recombinant mold strains free of bacterial DNA contamination.

Recently, a number of fungal species have also been transformed using heterologous prokaryotic and eukaryotic genes. Examples of heterologous expression in filamentous fungi include the expression of a bacterial phosphotransferase in *N. crassa, Dictyostellium discoideum* and *Cephalosporium acremonium*, and the high-yield production of melanin in *Streptomyces* transformed with bacterial tyrosinase (U.S. Pat.

No. 5,814,495 to della-Cioppa et al.). Berka et al. describe vectors for expression and secretion of heterologous proteins in filamentous fungi, devoid of bacterial DNA (U.S. Pat. No. 6,171,817 to Berka et al.). Using the vectors described, the authors produced transgenic *A. awamori* and *A. nidulans* expressing and secreting biologically active bovine chymosin, *A. niger* glucosamylase, and *M. miehei* carboxyl protease. Fungal transformation with high copy number (U.S. Pat. No. 6,090,574 to Giuseppin et al.) and over-expression of transformed genes (U.S. Pat. No. 6,403,362 to Moriya et al.) have also been reported recently. Thus, heterologous and homologous genes have been manipulated for increased production of desired gene products in filamentous fungi. However, none of the abovementioned methods have attempted to provide improved yields and longevity of fungal species by engineered enhancement of growth rate, extenuation of the vegetative growth phase in culture, enhanced spore production and improved resistance to environmental stress with heterologous gene products effecting programmed cell death and apoptosis.

There is thus a widely recognized need for, and it would be highly advantageous to have, methods and novel media for improving fungal growth processes such as vegetative development, fungal sporogenesis and sustainability in culture and storage as well as, fungal pathogenicity, using transformation and treatment of filamentous fungi with heterologous Bcl-2 sequences and proteins.

SUMMARY OF THE INVENTION

According to the present invention there is provided a filamentous fungus comprising an exogenous polynucleotide capable of expressing a Bcl-2 polypeptide or an active portion thereof, the filamentous fungus exhibiting accelerated growth as compared to a wild type filamentous fungus.

According to further features in preferred embodiments of the invention described below the filamentous fungus is any filamentous species within the Eumycota (true fungi) divisions Ascomycota, Basidiomycota, Zygomycota, or Chytridiomycota (e.g. Tree of Life, http://tolwebdot.org/tree.

According to still further features in the described preferred embodiments the filamentous fungus is *Colletotrichum gloeosporioides* f. sp. *Aeschynomene* (C.g.a).

According to yet further features in the described preferred embodiments the filamentous fungus exhibits accelerated conidia accumulation as compared to said wild type filamentous fungus when grown in solid medium.

According to further features in the described preferred embodiments the filamentous fungus exhibits extended biomass accumulation as compared to said wild type filamentous fungus when grown in liquid medium.

According to still further features in the described preferred embodiments the filamentous fungus remains viable in storage for a time period longer than said wild type filamentous fungus when grown on solid media.

According to yet further features in the described preferred embodiments the filamentous fungus exhibits increased resistance to temperature, oxidative and/or radiation stress as compared to said wild type filamentous fungus.

Further according to the present invention there is provided a method of enhancing growth and or pathogenicity of a filamentous fungus, the method comprising providing the filamentous fungus with a Bcl-2 polypeptide or an active portion thereof, thereby enhancing growth of the filamentous fungus.

According to further features in the described preferred embodiments the filamentous fungus is grown in a culture media selected from the group consisting of REG medium, EMS medium and Pea Juice medium and said Bcl-2 polypeptide or said active portion thereof is provided within said culture media.

According to still further features in the described preferred embodiments enhancing growth is accelerating conidia accumulation, and/or extending biomass accumulation and growth is determined by colony area.

Further according to the present invention there is provided a method of enhancing the viability of a filamentous fungus stored at sub-optimal temperature, the method comprising providing the filamentous fungus with a Bcl-2 polypeptide or an active portion thereof, thereby enhancing viability of the filamentous fungus stored at sub-optimal temperature.

According to further features in the described preferred embodiments the sub-optimal temperature is room temperature or 4° C., and said enhancing viability is increasing germination rate, increasing conidial production and/or decreasing melanin accumulation.

Further according to the present invention there is provided a method of increasing the resistance of a filamentous fungus to stress, the method comprising providing the filamentous fungus with a Bcl-2 polypeptide or an active portion thereof, thereby increasing resistance of the filamentous fungus to stress.

According to further features in the described preferred embodiments, said stress is temperature, oxidative and/or radiation stress.

According to further features in the described preferred embodiments said radiation stress is UV radiation, and said increased resistance is at least two fold lesser conidial mortality as compared to said wild type filamentous fungus.

According to yet further features in the described preferred embodiments, said oxidative stress is exposure to oxygen radical concentration equal to at least 0.05% (v/v) $H_2O_2$ concentration, and whereas said increased resistance is at least 100% greater colony area as compared to said wild type filamentous fungus.

According to yet further features in the described preferred embodiments the temperature stress is a temperature below or above 28° C. and said increased resistance is characterized by at least 50% greater growth rate.

According to still further features in the described preferred embodiments the step of providing is effected by expressing within the filamentous fungus an exogenous polynucleotide encoding said Bcl-2 polypeptide or said active portion thereof.

According to yet further features in the described preferred embodiments the exogenous polynucleotide comprises a promoter sequence operably linked to a nucleic acid sequence encoding said Bcl-2 polypeptide or said active portion thereof.

According to further features in the described preferred embodiments the promoter sequence is an *Aspergillus nidulans* gpdh promoter and said nucleic acid sequence is human Bcl-2.

According to still further features in the described preferred embodiments the step of providing is effected by exposing the filamentous fungus to said Bcl-2 polypeptide or said active portion thereof.

According to yet further features in the described preferred embodiments the Bcl-2 polypeptide or said active portion thereof is linked to a protein transduction domain for facilitating entry of said Bcl-2 polypeptide or said active portion thereof into the filamentous fungus.

According to further features in the described preferred embodiments the transduction domain is TAT According to still further features in the described preferred embodiments the step of exposing is effected under conditions suitable for protein transduction into the filamentous fungus.

According to yet further features in the described preferred embodiments the Bcl-2 polypeptide or said active portion thereof is cationized prior to said step of providing the filamentous fungus with said Bcl-2 polypeptide or an active portion thereof.

Further according to the present invention there is provided a fungal culture medium suitable for growth of fungus, the fungal culture medium comprising a Bcl-2 polypeptide or an active portion thereof and a carbon source.

According to further features in the described preferred embodiments the Bcl-2 polypeptide or an active portion thereof is linked to a protein transduction domain for facilitating entry of said Bcl-2 polypeptide or said active portion thereof into the filamentous fungus.

According to yet further features in the described preferred embodiments the protein transduction domain is a synthetic peptide.

According to still further features in the described preferred embodiments the transduction domain is TAT.

According to further features in the described preferred embodiments the Bcl-2 polypeptide or active portion thereof is cationized.

According to yet further features in the described preferred embodiments the Bcl-2 polypeptide or active portion thereof is an ethylenediamine cationized Bcl-2 polypeptide or active portion thereof.

According to another aspect of the present invention there is provided a method of eradicating an unwanted weed growing in a crop field, the method comprising spreading in the crop filed a filamentous fungus pathogenic to the unwanted weed, the filamentous fungus capable of expressing an exogenous polynucleotide encoding Bcl-2 or an active portion thereof in the crop field thereby eradicating the unwanted weed.

Figure 4:
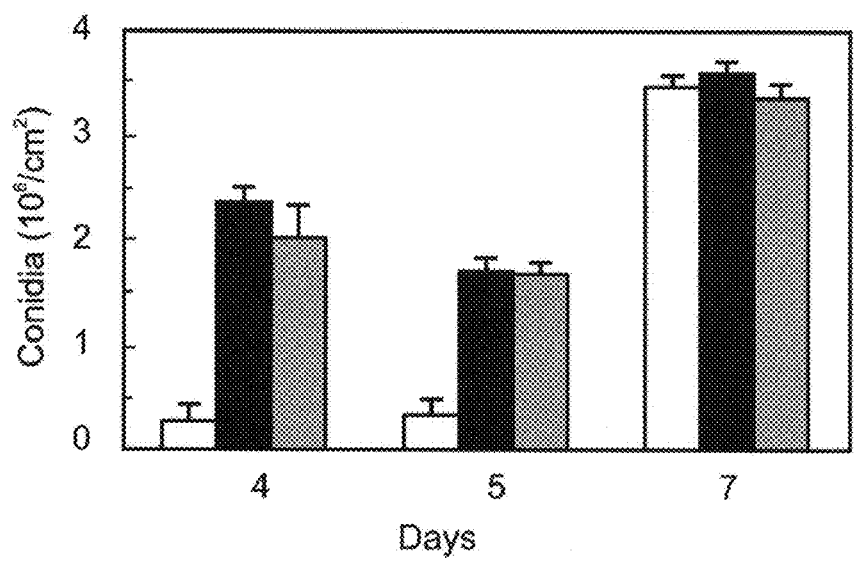

According to yet another aspect of the present invention there is provided a filamentous fungus comprising a first exogenous polynucleotide encoding Bcl-2 or an active portion thereof, and a second exogenous polynucleotide encoding a suicide gene.

According to yet another aspect of the present invention there is provided a method of producing a compound of interest comprising: (a) providing a filamentous fungus expressing a Bcl-2 polypeptide or an active portion thereof; and (b) culturing said filamentous fungus under conditions suitable for producing said compound of interest; and (c) isolating said compound of interest.

According to yet further features in the described preferred embodiments the compound of interest is naturally produced by the filamentous fungus.

According to yet further features in the described preferred embodiments the compound of interest a polypeptide expressed by the filamentous fungus.

According to yet further features in the described preferred embodiments the filamentous fungus is *Aspergillus niger*.

According to yet further features in the described preferred embodiments the compound is selected from the group consisting of an organic acid and an enzyme According to yet further features in the described preferred embodiments the organic acid is citric acid.

According to yet further features in the described preferred embodiments the enzyme is β-glucanase or pectinase.

The present invention successfully addresses the shortcomings of the presently known methods of enhancing fungal growth and pathogenicity by providing methods and media for transformation and treatment of filamentous fungi with heterologous Bcl-2 sequences and polypeptides. Filamentous fungi having Bcl-2 sequences exhibit greater viability in storage conditions, accelerated accumulation of biomass and superior resistance to stress as compared to wild type filamentous fungi.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

The patent or application file contains at least one drawing executed in color. Copies of this patent or patent application publication with color drawing(s) will be provided by the Office upon request and payment of the necessary fee.

FIGS. 1A-B are a graphic representation of the effect of expression of human Bcl-2 in two transgenic *C. gloeosporioides* isolates (#15 and #21) on biomass production in liquid REG medium. FIG. 1A represents fresh weight (in grams), and FIG. 1B dry weight (in grams) of mycelium, as a function of time post inoculation. Note the rapid peak of accumulation of biomass (at approx. 108 hours) of transgenic isolates 15 (closed squares) and 21 (closed triangles), compared to the wild type isolates (closed diamonds);

FIGS. 2A-B are a graphic representation of the effect of expression of human Bcl-2 in two transgenic *C. gloeosporioides* isolates (#15 and #21) on biomass production in liquid EMS medium. FIG. 2A represents fresh weight (in grams), and FIG. 2B dry weight (in grams) of mycelium, as a function of time post inoculation. Note the rapid peak of accumulation of biomass (at approx. 40 hours) of transgenic isolates 15 (closed squares) and 21 (closed triangles), compared to the wild type isolates (closed diamonds), and the significant advantage of the transgenic isolates at greater than 108 hours;

FIGS. 3A-B are a graphic representation of the effect of expression of human Bcl-2 in two transgenic *C. gloeosporioides* isolates (#15 and #21) on biomass production in liquid Pea Juice medium. FIG. 3A represents fresh weight in grams), and FIG. 3B dry weight (in grams) of mycelium, as a function of time post inoculation. Note the rapid growth peak (at approx. 40 hours) of transgenic isolates 15 (closed squares) and 21 (closed triangles), compared to the wild type isolates (closed diamonds);

FIG. 4 is a graphic representation of the effect of expression of human Bcl-2 in two transgenic *C. gloeosporioides* isolates (#15 and #21) on conidia production on liquid solid REG medium. The columns represent the average number of conidia/$cm^2$ per colony after 4 to 7 days growth. Note the rapid growth of conidia in colonies of transgenic isolates 15 (dark grey) and 21 (grey) at days 4 and 5, compared with wild type (open column);

FIGS. 5A-C are photographs depicting the effect of expression of human Bcl-2 in a transgenic *C. gloeosporioides* isolate (#21) on culture sustainability in cold. Wild type (FIGS. 5A and 5B) and transgenic (FIG. 5C, #21) isolates were grown for 5 days at 28° C. on REG medium, and transferred to 4° C. for up to 30 days. Note the loss of vitality in the wild type isolate at 5 (FIG. 5A) and 30 (FIG. 5B) days, compared with the maintenance of healthy morphology and pigmentation in the transgenic isolates at 30 days (FIG. 5C);

FIG. 6 is a graphic representation of the effect of expression of human Bcl-2 in two transgenic *C. gloeosporioides* isolates (#15 and #21) on resistance to temperature stress for growth on solid REG medium. Plates were inoculated with mycelial plugs of transgenic isolates 15 (closed squares) and 21 (closed triangles) and wild type isolates (closed diamonds), and grown at indicated temperatures for 5 days. Growth is expressed as radial colony area (in $cm^2$). Note the superior growth of the transgenic isolates at sub-optimal (<28° C.) and supra-optimal (>28° C.) temperatures compared to the wild type (broken line);

FIG. 7 illustrates infectivity of two Bcl-2 transgenic *C. gloeosporioides* isolates (#15 and #21) and of wild type isolate 6 days following plant inoculation. Plants were inoculated with a suspension containing $5\times10^3$ conidia/ml. Pictures were taken 6 days after inoculation;

FIGS. 8A-C illustrate enhanced levels of several stress induced genes in two Bcl-2 transgenic *C. gloeosporioides* isolates (#15 and #21) compared to their levels in the wild type isolate. FIG. 8A shows the level of a general stress-responsive gene, STI35 prior to and following a heat stress treatment at 32° C. Transcript level of STI35 is already induced in the Bcl-2 isolates even at the optimal temperature. FIG. 8B shows the transcript levels of catalase genes in transformed and wild type fungi cells grown in the presence or absence of 0.04% hydrogen peroxide. Only one catalase transcript is present in both the wild type and Bcl-2 isolates; the Bcl-2 isolates express another catalase gene of lower molecular weight that is absent in the wild type. FIG. 8C shows expression of a superoxide dismutase (SOD) encoding gene. Following a 4 h exposure to $H_2O_2$, transcript level in the wild type reached a similar level to that detected in the Bcl-2 isolates not exposed to $H_2O_2$. Expression of this gene is further enhanced in both wild type and Bcl-2 isolates following 24 hours of exposure to $H_2O_2$;

FIG. 9 illustrates *Aspergillus niger* transgenic isolates expressing human Bcl-2 gene. Total RNA from wild type and ten different transgenic isolates was extracted and probed with the human Bcl-2 gene. C-Total RNA from C.g.a. Bcl-2 transgenic isolate;

FIG. 10 graphically illustrates the effect of Bcl-2 expression in *Aspergillus niger* transgenic isolates on the resistance to oxidative stress;

FIG. 11 is a collection of photographs depicting the effect of Bcl-2 expression in *A. niger* isolates on resistance to oxidative stress; and FIGS. 12A-B illustrate biomass production enhancement in *Aspergillus niger* transgenic isolates expressing Bcl-2. FIG. 12A represents fresh weight in milligrams and FIG. 12B represents dry weight (in milligrams) of mycelium. Note the differences in the accumulated biomass between the wild type and the transgenic isolates.

DESCRIPTION OF THE PREFERRED EMBODIMENTS

The present invention is of modified filamentous fungi having enhanced growth and methods for the production thereof. Specifically, the present invention relates to the use of expressible polynucleotides and active polypeptides of the Bcl-2 family for producing fungal cells having superior accumulation of biomass, stress resistance and greater viability in cold storage, and the utilization of such modified fungal cells and cultures for enhancement of fungal growth, production of fungal metabolites, fungal proteins or improvement of production of heterologous proteins and metabolites in modified fungi.

The principles and operation of the present invention may be better understood with reference to the drawings and accompanying descriptions.

Before explaining at least one embodiment of the invention in detail, it is to be understood that the invention is not limited in its application to the details of components and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Filamentous fungi are used for a variety of industrial applications of great economic importance: food and drug production, the paper and pulp industry, agriculture, bioremediation and others. Although fungi can propagate on solid as well as liquid media, submerged liquid fermentation is presently the most common mode of large scale fungal culture. Despite constant efforts to improve fungal growth and yield, limited biomass production and sustainability of fungal cultures in fermentation remain a significant impediment to wider commercial utilization and greater availability of fungal products, metabolites and processes.

In animals, programmed cell death (PCD), or it's morphological equivalent, apoptosis, is genetically controlled cellular suicide, resulting in orchestrated disassembly of the cell in a non-inflammatory manner. Apoptosis in animals is controlled through functionally conserved genes, of the Bcl-2 family, having pro- and antiapoptotic character. Homologues such as Bcl-2, Bcl-$X_L$, Bcl-W, A1, MCL-1, E1B-19K, and BHRF-1 are characteristically anti-apoptotic, while expression of Bax, Bak, Bik, Bid, Bim, Bad and Bcl-G is associated with induction of cell death. The Bcl-2 family, and it's functional equivalents, exhibit well conserved, active binding (BH) domains that have been identified across broad taxonomic distances (for an exhaustive review of the role and mechanisms of Bcl-2 superfamily members in survival and cell death in eukaryotes, see Bomer, C. Mol Immunol. 2003, 39:615-47).

Transgenic plant and animal cells expressing regulators of apoptosis such as Bcl-2 and CED-9 have demonstrated enhanced resistance to pathogen challenge (Dickman et al. PNAS USA 2001;98:6957-62), UV irradiation and exposure to paraquat (Mitsuhara, et al. Curr. Biol 1999;9:775-78). It has been proposed that the pathogen resistance observed with expression of heterologous Bcl-2 family genes is a result of prevention of oxygen-induced cell death, inactivation of proapoptotic proteins, and sequestration of capsase-activating proteins.

Although the mechanisms and function of members of the Bcl-2 gene family have been studied extensively in yeast, such as *Sacchromyces cerevesiae* (see, for example, Gross et al. Mol. Cell. Bio 2000;20:3125-36), the effects of endogenous and heterologous regulators of apoptosis on growth and viability in filamentous fungi have not been investigated. The present inventors sought to identify and characterize these effects by introducing the anti-apoptotic human Bcl-2 gene into a commercially important filamentous fungus.

While reducing the present invention to practice, it was unexpectedly uncovered that transgenic strains of the commercially important filamentous fungus *C. gloeosporioides* f. sp. *aeschynomen*, modified to express the human Bcl-2 gene can be cultured in fermentation for substantially longer periods of time, and have enhanced growth rate and spore production. As a result of the expression of the heterologous gene, the transgenic fungi demonstrate a dramatic increase in fresh and dry biomass production in liquid cultures. Thus, the modified filamentous fungi can be used for improving yields of fungi, fungal metabolites or fungal related processes.

Thus, according to one aspect of the present invention there is provided a method of enhancing growth of a filamentous fungus. The method is effected by providing the filamentous fungus with a Bcl-2 polypeptide or an active portion thereof, thereby enhancing growth of the filamentous fungus.

Enhanced growth is characterized by accelerated conidia accumulation, and/or extended biomass accumulation, while growth is determined by colony area. Methods for determining conidial accumulation, biomass accumulation and colony area are well known to one of ordinary skill in the art. For example, conidia can be counted by direct observation using a microscope and any commercially available Hemocytometer Chamber, directly in liquid medium or in liquid medium after washing of cultures grown on solid media. As described in the Material and Methods section hereinbelow, conidial accumulation is expressed as density of conidia (conidia/$cm^2$). Biomass accumulation is determined by filtering cultures and measuring wet weight, or dry weight per culture volume, as described hereinbelow. Colony area is measured directly from the surface of fungal colonies grown in solid media.

Methods suitable for providing the filamentous fungus with Bcl-2 polypeptides are described in detail hereinbelow.

Methods for growth of filamentous fungi on solid and liquid medium are well known to one of ordinary skill in the art. For detailed description of methods for growth, storage, conidial harvesting and germination, preparation of media, etc, of a representative filamentous fungus (*A. nidulans*) see article by Kaminskyj, S., at www.fgsc.net. Culture media commonly comprise a source of carbon, preferably a carbohydrate source such as agar, peptone or nutrient broth. Additionally, salts, transition metals and other additives may be required for optimum growth. Fungal culture media are available commercially (for example, from MicroBioMedia, Dublin Ohio, USA). As described in detail hereinbelow, solid media include nutrients and agar, potato starch or any other suitable solidifying agent.

Preferably, the filamentous fungus is grown in a culture media selected from the group consisting of REG medium, EMS medium and Pea Juice medium and the Bcl-2 polypeptide or an active portion thereof is provided within the culture media. The preparation of REG medium, EMS medium and Pea juice medium is detailed in the Materials and Methods section hereinbelow. As detailed hereinabove, the Bcl-2 polypeptide or active portion thereof can be provided by simply adding the polypeptide to the abovementioned culture medium or by providing transformed fungus or other microorganism expressing and secreting the Bcl-2 polypeptide or active portion thereof in co-culture.

It will be appreciated that mycelium production in liquid fermentation is affected by the culture conditions. During fermentation fungi modify the medium by degrading and absorbing nutrients from the medium and by secretion of various ions, metabolites and enzymes to the medium. Growth and development are affected by the external conditions even before the nutrients become a limiting factor. Most significantly, pH changes and accumulation of toxic compounds are primary factors that limit productivity in fermentation. Surprisingly, while reducing the present invention to practice, it was uncovered that Bcl-2 delayed these effects. As is demonstrated in FIGS. 1A-B, 2A-B and 3A-B, and described in detail in Example I hereinbelow, transgenic filamentous fungi expressing Bcl-2 grew faster and continued to produce and accumulate new mycelium for extended periods of time compared to the wild type, accumulating between 2 to 2.5 times more biomass per culture.

In addition, the transgenic filamentous fungi expressing Bcl-2 of the present invention, produced significantly greater numbers of conidia at an early stage compared to the wild type, as demonstrated in FIG. 4 and described in detail in Example II hereinbelow. Without wishing to be limited by a single hypothesis, it appears as if the early production of conidia in the Bcl-2 isolates is under different regulation than natural conidia production that occurs later, since at 7 days both the wild type and Bcl-2 strains produced similar numbers of conidia.

The phrase "filamentous fungi" refers to all filamentous forms of the subdivision Eumycotina, (Alexopoulos, C. J. (1962), Introductory Mycology, New York: Wiley). These fungi are characterized by a vegetative mycelium with a cell wall composed in part of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In contrast, vegetative growth by yeasts such as *S. cerevisiae* is by budding of a unicellular thallus, and carbon catabolism may be fermentative. This developmental difference is reflected in the fact that the genome size of *S. cerevisiae* is $14\times10^6$ bp and it encodes approximately 6,000 genes, while filamentous fungi have much larger genomes (e.g. $27\times10^6$ bp in *N. crassa*, $37\times10^6$ bp in *Cochliobolus heterostrophus*, and $45\text{-}50\times10^6$ bp in *Colletotrichum* sp.) and the estimated number of genes is over 9,000. Since *S. cerevesiae* does not naturally develop complex structures such as hyphae, fruiting bodies, appressoria, or haustoria, it may not respond to environmental and internal signals in the same fashion as filamentous species, in which the manifestation of these complex process may require an active and well regulated plant cell death cascade. Moreover, gene expression and codon usage in fungi may be more closely related to plants and mammals than to yeasts. Illustrations of differences between *S. cerevisiae* and filamentous fungi include the inability of *S. cerevisiae* to process *Aspergillus* and *Trichoderma* introns and the inability to recognize many transcriptional regulators of filamentous fungi (Innis, M. A. et al. (1985) Science, 228, 21-26).

Various species of filamentous fungi may be used as expression hosts including the following genera: *Aspergillus, Trichoderma, Neurospora, Penicillium, Cephalosporium* (anamorph *Penicillium*), *Achlya, Podospora, Endothia, Mucor, Cochliobolus* and *Pyricularia*. Specific expression hosts include *A. nidulans*, (Yelton, M., et al. (1984) Proc. Natl. Acad. Sci. USA, 81, 1470-1474; Mullaney, E. J. et al.

(1985) Mol. Gen. Genet. 199, 37-45; John, M. A. and J. F. Peberdy (1984) Enzyme Microb. Technol. 6, 386-389; Tilburn, et al. (1982) Gene 26, 205-221; Ballance, D. J. et al., (1983) Biochem. Biophys. Res. Comm. 112, 284-289; Johnston, I. L. et al. (1985) EMBO J. 4, 1307-1311), *A. niger*, (Kelly, J. M. and M. Hynes (1985) EMBO 4, 475-479), *A. awamori*, e.g., NRRL 3112, ATCC 22342, ATCC 44733, ATCC 14331 and strain UVK 143f, *A. oryzae*, e.g., ATCC 11490, *N. crassa* (Case, M. E. et al. (1979) Proc. Natl. Acad. Scie. USA 76, 5259-5263; Lambowitz U.S. Pat. No. 4,486,553; Kinsey, J. A. and J. A. Rambosek (1984) Molecular and Cellular Biology 4, 117-122; Bull, J. H. and J. C. Wooton (1984) Nature 310, 701-704), *Trichoderma reesei*, e.g. NRRL 15709, ATCC 13631, 56764, 56765, 56466, 56767, and *Trichoderma viride*, e.g., ATCC 32098 and 32086. Cultures of filamentous fungi are available from the American Type Culture Collection (Rockville, Md., USA). In one embodiment, the expression host is an engineered fungus. U.S. Pat. No. 6,432,672 describes a filamentous fungus with a DNA domain suitable for integration of one or more copies of a recombinant DNA molecule. A preferred expression host is *Colletotrichum gloeosporioides* f. sp. *aeschynomene*, a filamentous fungus used for production of the biological weed control agent Collego® (Encore Technologies, Minnesota, USA).

As used herein, the term "Bcl-2 polypeptide or active portion thereof" refers to a polypeptide of the Bcl-2 superfamily which includes at least one of BH1, BH2, BH3 or BH4 binding domains and which exhibits a growth enhancing activity when expressed in eukaryotic cells. Examples of genes encoding proteins of the Bcl-2 family include the mammalian bcl-2 (GenBank Accession No: AAA35591, from human), bax (GenBank Accession Nos: Q07812, human isoform A, Q07814, human isoform B, and Q07815, human isoform C), bcl-2A1 (GenBank Accession No: NP_004040 from human), bcl-W (GenBank Accession No: NP_004041 from human), bcl-2L1 (GenBank Accession No: NP_612815), bcl-2L2 (GenBank Accession No: NP_001182 from human), bad (GenBank Accession No: NP_004313 from human), bak (GenBank Accession No: NP_001179 from human), MCL-1 (GenBank Accession No: Q07820 from human) genes, CED-9 from *C. elegans* (GenBank Accession No: A53189), the human adenovirus E1B-19K gene (GenBank Accession No: NP_040848) the BHRF1 gene (derived from Epstein-Barr virus) and the LMW5-HL gene (derived from African Swine Fever virus) (Takayama et al. Experimental Medicine, 1995;13: 24-31). It will be appreciated, in the context of the present invention, that although certain proteins and protein homologues of the Bcl-2 superfamily are characterized by pro-apoptotic activity in their native form, portions of these proteins (such as the BH1 and BH2 domains) can be effective for growth enhancement and as such may be suitable for use in transforming filamentous fungi. Further, peptide fragments of Bcl-2 polypeptides having anti-apoptotic and growth enhancing activity may be identified, and can be synthesized for use in the methods and transformed filamentous fungus of the present invention.

Several approaches can be used to provide Bcl-2 or the active portion thereof to cultured fungal cells.

Exogenous polynucleotides expressing a Bcl-2 polypeptide (see Genbank accession citations) or active portion thereof can be introduced into filamentous fungus for transient expression or integration into the fungal genome and stable, heritable expression. Appropriate fungal cells can be transfected with an appropriate transfer vector containing the polynucleotide encoding a Bcl-2 polypeptide or active portion thereof. Alternatively, nucleic acid molecules comprising the polynucleotide encoding the Bcl-2 polypeptide or active portion thereof may be introduced into the host fungus using traditional methods such as transformation using calcium phosphate precipitation (Dubensky et al., PNAS 81:7529-7533, 1984), direct microinjection of such nucleic acid molecules into intact target cells (Acsadi et al., Nature 352:815-818, 1991), and electroporation whereby cells suspended in a conducting solution are subjected to an intense electric field in order to transiently polarize the membrane, allowing entry of the nucleic acid molecules. Other procedures include *Agrobacterium* Ti plasmid-mediated transformation (as detailed in U.S. Pat. No. 6,255,115 to Beijeresbergen et al, described hereinabove), microprojectile bombardment (Williams et al., PNAS 88:2726-2730, 1991), and the use of polycation compounds such as polylysine and receptor specific ligands. Examples of transformation with Bcl-2 and Bcl-2 homologues, and their expression in the transgenic cells include U.S. Pat. No. 6,436,393 to Bilbao et al. (human Bcl-2); U.S. Pat. No. 6,310,272 to Ohasi et al. (human BCI-$X_L$); U.S. Pat. No. 6,015,687 to Keifer (human CDN protein, a Bcl-2 homologue) and Dickman et al. (PNAS USA 2001;98:6957-62 (human Bcl-2, BCI-$X_L$ and *C. elegans* CED-9).

Thus, according to one preferred embodiment of the present invention, the step of providing the Bcl-2 or portion thereof is effected by expressing within the filamentous fungus an exogenous polynucleotide encoding said Bcl-2 polypeptide or an active portion thereof. In a yet more preferred embodiment the exogenous polynucleotide comprises a promoter sequence operably linked to a nucleic acid sequence encoding said Bcl-2 polypeptide or an active portion thereof.

Exogenous polynucleotides comprising the entire coding sequence of the Bcl-2 gene, for example from nucleotide coordinates 32 to 751 of the human Bcl-2 gene (GenBank Accession No. M14754) can be expressed in method of the present invention. However, exogenous polynucleotides encoding specific active portions thereof, such as the BH1 domain (amino acid coordinates 136-151) and/or the BH2 domain (amino acid coordinates 183-198) of the human bcl-2 protein (Genebank Accession No. AAA 35591) can also be expressed for enhancing growth in filamentous fungi.

Constructs suitable for transformation of fungi and the expression of heterologous proteins in transformed filamentous fungi are well known in the art, and have been extensively described. U.S. Pat. Nos. 6,171,817 and 6,103,490 to Berka et al. and U.S. Pat. No. 6,130,063 to Lawlis et al. describe constructs comprising sequences encoding bovine chymotrypsin, or fusion precursors in which sequences encoding *A. niger* glucoamylase and bovine prochymotrypsin were fused, under the control of 5' and 3' regulatory sequences of the *A. niger* glucoamylase gene, for expression and secretion of the exogenous sequences in a number of *Aspergillus* species. Expression and secretion of *H. grisae* glucoamylase, and other heterologous proteins fused with regulatory sequences from other fungal species (e.g. *M. miehei*), demonstrated that *Aspergillus* species can recognize heterologous control elements as well as coding sequences. U.S. Pat. No. 5,945,328 to Woldike et al. describes transformation of *A. oryzae* with vectors comprising human trypsinogen I and II, and porcine trypsin coding sequences and fungal regulatory sequences, and the expression of detectable levels of catalytic activity and enzyme protein in the transformants. For increased expression of heterologous proteins, Watanabe (International Publication No. WO 01/18219) constructed a vector comprising promoter and termination sequences of the filamentous fungus Agonomycetales. Fungal expression vectors, carrying the fungal bar selectable marker, multiple unique restriction sites, and the *N. crassa* or *A. nidulans* promoter sequences are available through the Fungal Genetics Stock Center (FGSC, Dept of Microbiol, Univ. of Kansas, Kansas City, Kans., USA). In a preferred embodiment, the DNA construct is a polynucleotide vector containing a promoter sequence operably linked to a nucleic acid sequence encoding a Bcl-2 polypeptide or an active portion thereof. It will be appreciated that such constructs for transformation comprise, in addition, fungally active terminator sequences (including polyadenylation sequences) which are recognized by the filamentous fungus in which expression occurs. When recognized by the host, the stop signal terminates translation of the mRNA encoding the heterologous Bcl-2 polypeptide. The thus constructed vectors are used to transform a filamentous fungus. The gSBcl2 vector described in detail in Materials and Methods of the Examples section hereinbelow is an example of one expression vector suitable for use with the present invention.

As used herein, the phrase "promotor sequence" refers to a DNA sequence which is recognized by the particular filamentous fungus for expression purposes. It is operably linked to a DNA sequence encoding the above defined Bcl-2 polypeptide. Such linkage comprises positioning of the promoter with respect to the translation initiation codon of the DNA sequence encoding the Bcl-2 DNA sequence. The promoter sequence contains transcription and translation control sequences which mediate the expression of the Bcl-2 DNA sequence. Examples include the promoter from the *A. awamori* or *A. niger* glucoamylase genes (Nunberg, J. H. et al. (1984) Mol. Cell. Biol. 4, 2306-2315; Boel, E. et al. (1984) EMBO J. 3, 1581-1585), the *Mucor miehei* carboxylprotease gene, the *Trichoderma reesei* cellobiohydrolase I gene (Shoemaker, S. P. et al. (1984) European Patent Application No. EP 00137280 A1), the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 3745) the *A. nidulans* alcA gene (Lockington, R. A. et al. (1986) Gene 33, 137-149), the *A. nidulans* tpiA gene (McKnight, G. L. et al. (1986) Cell 46, 143-147), the *A. nidulans* amdS gene (Hynes, M. J. et al. (1983) Mol. Cell Biol. 3, 1430-1439), and higher eukaryotic promoters such as the SV40 early promoter (Barclay, S. L. and E. Meller (1983) Molecular and Cellular Biology 3, 2117-2130).

Likewise a "terminator sequence" is a DNA sequence which is recognized by the expression host to terminate transcription. It is operably linked to the 3' end of the Bcl-2 DNA encoding the Bcl-2 polypeptide to be expressed. Examples include the terminator from the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 37-45), the *A. awamori* or *A. niger* glucoamylase genes (Nunberg, J. H. et al. (1984) Mol. Cell. Biol. 4, 2306-253; Boel, E. et al. (1984) EMBO J. 3, 1581-1585), and the *Mucor miehei* carboxylprotease gene (EP Publication No. 0 215 594), although any fungal terminator is likely to be functional in the present invention.

A "polyadenylation sequence" is a DNA sequence which when transcribed is recognized by the expression host to add polyadenosine residues to transcribed mRNA. It is operably linked to the 3' end of the Bcl-2 DNA encoding the Bcl-2 polypeptide to be expressed. Examples include polyadenylation sequences from the *A. nidulans* trpc gene (Yelton, M. et al. (1984) Proc. Natl. Acad. Sci. USA 81, 1470-1474; Mullaney, E. J. et al. (1985) Mol. Gen. Genet. 199, 37-45), the *A. awamori* or *A. niger* glucoamylase genes (Nunberg, J. H. et al. (1984) Mol. Cell. Biol. 4, 2306-2315) (Boel, E. et al. (1984) EMBO J. 3, 1581-1585), and the *Mucor miehei* carboxylprotease gene described above. Any fungal polyadenylation sequence, however, is likely to be functional in the present invention.

Following transformation of the host filamentous fungus with the expression vector, viable transformants can be identified by screening for the expression of the heterologous Bcl-2 polypeptide or active portion thereof. Such screening may be via immunogenicity of Bcl-2 protein epitopes, using specific antibodies, separation of fungal proteins using, for example, gel electrophoresis, HPLC or affinity chromatography, or biological activity of the expressed Bcl-2 proteins (such as, for example, complementary binding of BH domains).

Alternatively, an expressible selection characteristic may be used to isolate transformants by incorporating DNA sequences encoding the selection characteristic into the transformation vector. Examples of such selection characteristics include resistance to various antibiotics, (e.g., hygromycin B, aminoglycosides, benomyl etc.) and sequences encoding genes which complement an auxotrophic defect (e.g. pyr4 complementation of pyr4 deficient *A. nidulans, A. awamori* or *C. gloeosporioides* or ArgB complementation of ArgB deficient *A. nidulans* or *A. awamori*) or sequences encoding genes which confer a nutritional (e.g., acetamidase) or morphological marker (e.g. green fluorescence protein—GFP) in the expression host.

Expression of the Bcl-2 polypeptide or active portion thereof may be constitutive or inducible, in accordance with the promoter chosen for the expression vector. As described hereinabove, several regulatory fungal promoters have been successfully used to control the expression of heterologous proteins in transformed fungi. While reducing the present invention to practice, it was uncovered that expression of Bcl-2 in transformed filamentous fungus confers increased resistance to stress, enhanced growth at sub-optimal temperatures and greatly improved viability in storage at room temperature and cold. Thus, promoters known to be sensitive to signals related to sub-optimal temperature and stress in fungus, such as promoters of heat shock proteins can be used to activate expression of the Bcl-2 or active portion thereof only when the fungus is exposed to such sub-optimal or stressful conditions. Similarly, inhibition of Bcl-2 expression can be effected, if desirable, by using repressor elements functioning in filamentous fungus. Such conditional regulation of Bcl-2 expression can provide improved efficiency and economy of growth and culture of the transgenic fungi.

Although expression of Bcl-2 or portions thereof in fungal cells is preferred, the step of providing Bcl-2 or portions thereof can also be effected by exposing the fungal cells to this polypeptide.

Biologically active polypeptides, or portions thereof, may be delivered in an active form into cells, modulating biochemical processes of the target cells. In one method of protein transduction, the desired protein is fused to one or more peptide protein transduction domains (PTDs) from proteins capable of translocation into the cytosol or nucleus, such as the TAT domain from HIV, the *Drosophila antenapedae* PTD (Derossi et al., J Biol Chem 1996; 271:18188-93) or the HSV VP22 peptide. PTDs, which are important for secretion of proteins, have also been shown to improve translocation of fusion proteins across target cell membranes in vitro and in vivo. In one example, Davidson et al. (International Publication No. WO 02/055684) disclosed fusion proteins comprising lysosomal enzymes fused to a PTD motif, for improved uptake into cells and transit of the blood brain barrier, in the treatment of lysosomal storage disease. Also disclosed were DNA constructs encoding such fusion proteins. Similarly, Dowdy (U.S. Pat. No. 6,221,335 and International Publication No. WO 02/0555684 A2 to Dowdy) disclosed an antipathogen system for delivering cytotoxic proteins (such as caspase) to target cells comprising recombinant fusion proteins having conjugated cytotoxic and PTD (HIV TAT) sequences.

Thus, the Bcl-2 polypeptide or active portion thereof of the present invention may be provided by exposing the filamentous fungus to a Bcl-2 polypeptide or said active portion thereof linked to a protein transduction domain for facilitating entry of the Bcl-2 polypeptide or active portion thereof into the filamentous fungus. Examples of suitable PTDs are the TAT domain from HIV, the *Drosophila* antenapedae PTD and the HSV VP22 peptide. In a preferred embodiment, the protein transduction domain is TAT (GenBank Accession No. BAC45028).

Linkage or conjugation of the Bcl-2 polypeptide or active portion thereof to the PTD motif may be via chemical means, or most preferably effected by expression of a recombinant fusion protein expressed in a suitable host, as described in the abovementioned prior art references. Such a Bcl-2-PTD conjugate can be added to the culture media in effective concentrations, determined simply by measuring the uptake of fusion proteins into the fungal cells, and the resultant change in growth rate, viability and sustainability in storage. Using the fungal expression vectors described herein in detail, a population of filamentous fungus can be transformed to express such a Bcl-2-PTD fusion protein, and co-cultured with un-transformed fungus to provide the Bcl-2 polypeptide or portions thereof to the culture media (for examples of coculture of filamentous fungus, see Garcia-Kirchner et al. Mycopathologia 2002,154:85-91 and U.S. Pat. No. 5,866,380 to Lesage-Meessen et al, which discloses the coculture of fungal species *Actinomycetes, Ascomycetes* and *Basidomycetes*).

Another method of protein transduction is based on the observation that cationized proteins added to culture medium can be transduced into the cytosol of cells in a receptor- and transporter-independent manner. Futami et al. (J Biochem Tokyo 2002,132:223-28) describes the cationization of RNAse enzymes by modifying carboxyl groups with ethylenediamine, and detection of enzyme protein, catalytic activity and a strong cytotoxic effect in a variety of cells transduced with the cationized enzyme.

Thus, the Bcl-2 polypeptide or active portion thereof of the present invention may be provided by exposing the filamentous fungus to a Bcl-2 polypeptide or an active portion thereof under conditions suitable for protein transduction. In one preferred embodiment, the Bcl-2 polypeptide or an active portion thereof is cationized prior to said step of providing. The Bcl-2 polypeptide or active portion thereof can be cationized using the ethylenediamine method of Futami et al., in which a mild carbodiimide reaction is used to generate catalytically active yet optimally cationized polypeptides, or, alternatively, using the commercially available BioPORTER® Protein Delivery System (Sigma-Aldrich, St Louis Mo., USA). Cationized Bcl-2 polypeptides can be added directly to liquid or solid medium.

Thus, according to another aspect of the present invention there is provided a fungal culture medium suitable for growth of fungus, the fungal culture medium comprising a Bcl-2 polypeptide or an active portion thereof and a carbon source.

In a preferred embodiment the Bcl-2 polypeptide or an active portion thereof is linked to a protein transduction domain for facilitating entry of the Bcl-2 polypeptide or an active portion thereof into the filamentous fungus.

In another preferred embodiment the protein transduction domain is a synthetic peptide, such as TAT or any other PTD. Proteins containing suitable PTD motifs are described in detail hereinabove.

In a more preferred embodiment the Bcl-2 polypeptide or active portion thereof is cationized, most preferably by ethylenediamine cationization.

A suitable medium for growing the filamentous fungus of the present invention is Emerson's (EMS) medium containing (per 1 liter) 4 g yeast extract, 2 g soluble starch, 2.5 g $Na_2HPO_4$ and 0.5 g $MgSO_4.7H_2O$. The preparation of additional suitable media, such as REG medium and Pea juice medium is detailed in the Materials and Methods section hereinbelow. Fungal culture media are available commercially (for example, from MicroBioMedia, Dublin Ohio, USA). As described in detail hereinbelow, solid media include nutrients and agar, potato starch or any other suitable solidifying agent.

According to further features in the described preferred embodiments the filamentous fungus is grown in a culture media selected from the group consisting of REG medium, EMS medium and Pea Juice medium and the Bcl-2 polypeptide or an active portion thereof is provided within the culture media. As detailed hereinabove, the Bcl-2 polypeptide or active portion thereof can be provided by simply adding the polypeptide to the abovementioned culture medium or by providing transformed fungus or other microorganism expressing and secreting the Bcl-2 polypeptide or active portion thereof in co-culture.

The enhanced growth characterizing the fungal cultures of the present invention is characterized by accelerated conidia accumulation, and/or extended biomass accumulation and typically results in a substantial increase in colony area.

Methods for determining conidial accumulation, biomass accumulation and colony area are well known to one of ordinary skill in the art. For example, conidia can be counted by direct observation using a microscope and any commercially available Hemocytometer Chamber, directly in liquid medium or in liquid medium after addition of liquid to cultures grown on solid media. As described in the Material and Methods section hereinbelow, conidial accumulation is expressed as density of conidia (conidia/$cm^2$). Biomass accumulation is determined by filtering cultures and measuring wet weight, or dry weight per culture volume, as described hereinbelow. Colony area is measured directly from the surface of fungal colonies grown in solid media.

Figures 5A, 5B, 5C:
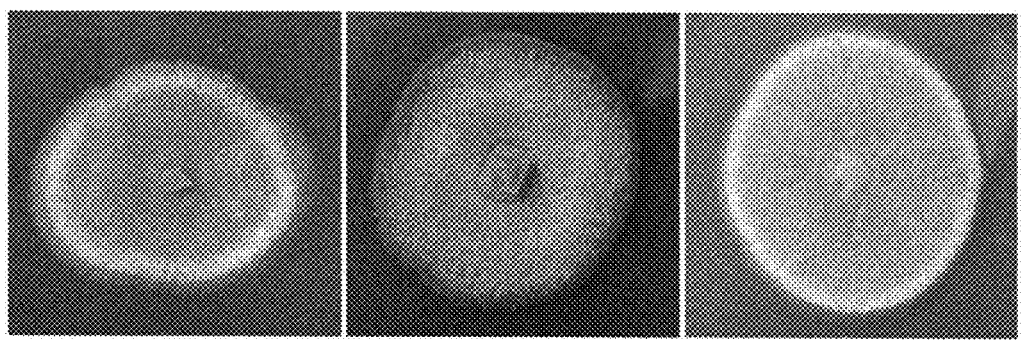

Cultures of wild type filamentous fungi are sensitive to sub-optimal conditions, and quickly lose vitality in, for example, cold conditions. Recovery of viable conidia from cultures following storage in cold or room temperature is thus a significant concern for culturing of filamentous fungus. While reducing the present invention to practice, it was uncovered that the expression of Bcl-2 in transgenic fungus improved sustainability in cold and room temperature, as demonstrated in FIGS. 5A-C and described in detail in Example III hereinbelow. Clearly, the wild type fungal colonies did not survive storage in cold or at room temperature, while conidia of the transformed filamentous fungus do not die when left at room temperature for periods of four weeks and even longer, cultures do not accumulate melanin and continue to sporulate and grow at 4° C. for over a year while the wild type strain ceased growth and senesced after less than two weeks in cold.

Thus, according to another aspect of the present invention there is provided a method of enhancing the viability of a filamentous fungus stored at sub-optimal temperature.

The method is effected by providing the filamentous fungus with a Bcl-2 polypeptide or an active portion thereof, thereby enhancing viability of the filamentous fungus stored at sub-optimal temperature.

As used herein, the phrase "sub-optimal temperature" refers to a temperature selected from a range of 2-25° C., preferably 3-20° C., more preferably, 3-15° C., most preferably 4-10° C., and enhanced viability manifests as an increase in germination rate, an increase in conidial production and/or a decrease in melanin accumulation. Methods for determining conidial production and melanin accumulation are well known to one of ordinary skill in the art. As described hereinbelow, conidial production can be determined by counting of conidia in stored cultures, and transfer to solid agar media in optimal growth conditions, and recording viable colonies. Germination rate is the proportion of conidia giving rise to viable colonies following inoculation or plating. Melanin accumulation (black color, as compared with orange color characteristic of healthy *C. gloeosporiodes*, for example) indicates senescence of the cultures.

Anti-apoptotic Bcl-2 and Bcl-2 homologues are known to prevent activation of senescence and cell death pathways following alterations of culture conditions, and have been shown to confer enhanced UV and chemical stress resistance when expressed in heterologous host cells (see, for example, Mitsuhara, et al. Curr. Biol 1999;9:775-78). However, the effect in filamentous fungus has not been investigated. While reducing the present invention to practice, transgenic filamentous fungus *C. gloeosporiodes* expressing human Bcl-2 were exposed to a variety of sub-optimal temperatures, UV radiation (254 nm, 12.5 Kj/cm$^2$), and oxygen stress (0.03-0.1 mM $H_2O_2$). As demonstrated in FIG. 6 and described in detail in Example IV hereinbelow, Bcl-2 conidia are at least two times more tolerant than wild type fungus to UV irradiation and oxygen stress and their growth is less affected at limiting temperatures.

Thus, according to yet another aspect of the present invention there is provided a method of increasing the resistance of a filamentous fungus to temperature, oxidative and/or radiation stress.

The method is effected by providing the filamentous fungus with a Bcl-2 polypeptide or an active portion thereof, thereby increasing resistance of the filamentous fungus to temperature, oxidative and/or radiation stress.

One form of radiation which negatively effects fungal viability and growth rate is UV radiation. A dose of 12.5 kJ/cm$^2$ of 254 nm radiation can induce 99% or more conidial mortality in wild type fungus. Providing the filamentous fungus with Bcl-2 polypeptide or an active portion thereof can substantially decrease radiation damage and lead to conidial mortality up to two fold lower than that of wild type filamentous fungus grown under identical conditions.

Temperatures higher than 28° C. negatively effect growth and viability of wild type filamentous fungi. Providing the filamentous fungus with Bcl-2 polypeptide or an active portion thereof can substantially decrease temperature damage and lead to conidial mortality up to 150% lower than that of wild type filamentous fungus grown under identical conditions.

Oxidative stress, resulting in free radical accumulation, is a significant danger to all organisms. All stages of fungal development are susceptible to oxidative stress in excess of the cell's endogenous antioxidant defenses. Oxidative stress such as exposure to 0.05% v/v $H_2O_2$ can reduce wild type filamentous fungal growth by up to 60%. Providing the filamentous fungus with Bcl-2 polypeptide or an active portion thereof can substantially decrease such oxidative damage and sustain normal growth rates at 0.05% v/v $H_2O_2$ and greater.

Filamentous fungi of the present invention expressing, or transduced with a Bcl-2 polypeptide or active portion thereof, having accelerated growth, greater sustainability in storage and increased resistance to stress hold great potential for improved utilization of fungi in solid and liquid fermentation and for biological control applications. Applications extend beyond biomass production and include any process that utilizes fungal material, fungal metabolites and proteins, fungus for bioremediation (see, for example, U.S. Pat. No. 5,877,014 to Shetty et al.) or biotechnological processes in which fungi are used for production of heterologous proteins. For example, maximal yields of enzymes from fungal cultures expressing recombinant proteins such as phytase (U.S. Pat. No. 6,350,602), dextranase (U.S. Pat. No. 6,156,553), cellulase (U.S. Pat. No. 6,017,870) and xylanase (U.S. Pat. No. 6,080,567) can be achieved more rapidly and cost-effectively. Additional fungal products whose production may be improved by the methods of the present invention include β-lactams and non-β-lactam antibiotics, cyclosporin A from *Tolypocladium* sp., vitamins, flavors, carotenoids and gibberellic acid. Specifically, as demonstrated in the Examples section, the filamentous fungi of the present invention expressing the Bcl-2 polypeptide or active portion thereof, can provide superior yields of bionematocides, bioinsecticides, biofungicides and bioherbicides such as the bioherbicide Collego®.

As is shown in the Examples section which follows, Bcl-2 expression in *C. gloeosporioides* enhanced virulence and pathogenicity (and thus the weed killing function) of this fungus thereby clearly indicating that expression of Bcl-2 in pathogenic filamentous fungi can be utilized to generate improved weed biocontrol agents.

Enhancing the virulence of biocontrol fungi holds great potential for product improvements. Many attempts to commercially utilize biocontrol agents have failed because of insufficient control, even with high inoculum levels (Gressle J., 2001, TRENDS in Biotechnol. 19: 149-154). Hypervirulence has been used in a range of microorganisms as a way to enhance biocontrol efficacy (reviewed in St. Leger and Screen, Genetic improvement of fungi for insect and weed control. In Fungal Biocontrol Agents—Progress, Problems and Potential (Butt, T M et al., eds) CABI publishing, Willingford, UK). Hypervirulence can be obtained by affecting any of a series of parameters including rapidity of infection establishment, lowering inoculum levels, requirement for humidity, ability to infect aged organisms or speed of progression through infected tissues. Enhancement of biocontrol agents through genetic engineering have been demonstrate only in a few cases in which known virulence genes were introduced and expressed in an insect or a weed biocontrol fungus (St. Leger et al., 1996, PNAS 93: 6349-54; Amsellem et al., 2002, Nature Biotechnol 20: 1035-39). Rendering the fungus more virulent to its host, and potentially to other, non host targets, enhance the efficacy of the product and increase its commercial value. In most cases where products failed to reach a commercial level the main obstacle was insufficient virulence which necessitates the use of extremely high inoculum and/or does, that do not always provide complete control of the target organism (Gressle J., 2001, TRENDS in Biotechnol. 19: 149-154; Gressle J. 2003, ASM News 69:498-502).

The use of hypervirulent transgenic fungi for field application requires that fail safe mechanisms are employed to prevent horizontal and diagonal gene transfer and to provide users with ways of preventing uncontrollable spread of the modified fungus. A number of strategies for controlling spread of transgenic organisms have been suggested (see, for example, Gressle 2001 Ibid). These include introduction of toxic or disadvantageous genes under inducible promoters that can be triggered by external application of specific chemicals (so called suicide vectors), flanking the target gene with "mitigating" genes which will render a potential acceptor-less fit, suppression of mating ability and/or conidiation, use of auxotroph mutants.

Examples of potential mitigation genes are provided in the literature and in Table 1 below.

TABLE 1

| Gene | Organism | Accession and GI |
|------|----------|------------------|
| fluG | Aspergillus nidulans | AACD01000081.1 GI: 29570934 |
| brlA | Aspergillus fumigatus | AY327894.1 GI: 37594599 |
| abaA | Penicillium marneffei | AY078193.1 GI: 28627560 |
| acr1 | Magnaporthe grisea | AB096705.1 GI: 25815189 |
| argB | Aspergillus nidulans | M29819.1 GI: 168016 |
| trpC | Aspergillus nidulans | X02390.1 GI: 2422 |
| rasA | Aspergillus fumigatus | AY327892.1 GI: 37594595 |
| alcA | Aspergillus nidulans | S47331.1 GI: 257921 |
| nia | Magnaporthe grisea | AY268083.1 GI: 30271888 |
| th1 | Aspergillus oryzae | BAC87839.1 GI: 34850418 |

For example, mating infertile strains can be generated by deletion of mating genes according to published protocols (e.g. Turgeon B G 1998, Ann Rev Phytopathol 36:15-37; Chang and Staben, 1994, Genetics 138:75-81). Conidiation can be suppressed by mutations or deletions in a range of genes that are necessary for spore formation and viability e.g. fluG, br/a abaA, acr1 (Lee and Adams, 1996, EMBO J. 15:299-309; Yamada et al., 1999, J Biosci Bioeng 87:424-9; Sewall et al., 1990, Plant Cell 2:731-9; Lau and Hamer 1998, Fung Genet Biol 24:228-239). Auxotrophs can be easily generated by mutating or deleting genes such as, argB and trpC which are involved in amino acid synthesis. Modifications in a wide range of genes which encode, for example, cell wall proteins, sugar and amino acid transporters, house keeping proteins, signal transduction components, melanin synthesis enzymes and appressoria formation components can be utilized to reduce fungal fitness.

Transgenic fungal lines can be generated with silent expression cassettes in which genes are introduced either in sense or antisense orientation under an inducible promoter that is activated by application of an external inducer, when the fungus reaches a certain developmental stage, or when it is grown under specific environmental conditions. Activation of the promoter will lead to production of a protein or RNA molecule which affects growth (e.g., dominant active rasA), metabolism and growth (e.g., anti sense or RNAi forms of metabolic and cell wall genes) or plant infection capabilities (appressoria-specifc genes, melanin, hydrophobins). Alternatively, a mutation might be introduced in an essential gene, for example, one which is required for amino acid synthesis. The corresponding gene can then be introduced back into the fungus under the transcriptional control of a promoter that can be suppressed by an external signal. The fungus will be viable only as long as the promoter that drives transcription of the transgene is active. Potential promoters for such applications include the alcA promoter which is induced by low levels of ethanol, the nia promoter which is activated by low nitrate levels, or promoters of the quinick acid and thiamine synthase genes that are suppressed by quinick acid and thiamine, respectively.

Yet another important use of the transformed fungi and fungi cultures of the present invention is in producing commercially important substances such as organic acids or polypeptides either naturally expressed by the fungi or expressed from exogenous constructs. For example, *Aspergillus niger* is used extensively for the production of organic acids, particularly citric acid, as well as extracellular enzymes, such as glucoamylase, α-glucanase and pectinase. Moreover, the ability of this filamentous fungus to secrete large amounts of extracellular protein has made it a prime candidate for the development of expression and secretion systems for heterologous proteins of pharmaceutical and industrial interest.

Thus, according to another aspect of the present invention there is provided a method of producing a substance of interest. The method is effected by culturing the Bcl-2 expressing filamentous fungi, or the filamentous fungi culture which includes Bcl-2 under conditions suitable for synthesis of the substance of interest (e.g., chemicals, polypeptides or polynucleotides). Following a predetermined culturing period, the substance is isolated from the culture (in the case of secreted substances) or extracted from the cells.

Examples of substances which can be produced in filamentous fungi, and the preferred filamentous fungi for production are listed below.

(i) β-lactams antibiotics such as penicillin, mainly produced by *Penicillium chrysogenum* and cephalosporin C produced by *Acremonium chrysogenum*.

(ii) Immunosuppressants such as cyclosporin A produced mainly by *Tolypocladium inflatum*.

(iii) Ergot alkaloids produced for biotechnological applications mainly by *Claviceps purpurea*, *C. paspali*, and *C. fusiformis*.

(iv) Phytohormones such as abscisic acid produced by *Botrytis cinerea* or gibberellins produced by *Gibberella fujikuroi*.

(v) Organic acids such as citric acid produced mainly by *Aspergillus niger*, itaconic acid produced mainly by *Aspergillus terreus*, and fumaric acid produced by *Rhizopus oryzae*.

(vi) Vitamins such as riboflavin (B2) produced by *Ashbya gossypii*.

(vii) Enzymes such as amylases produced by *Aspergillu oryzae*, glucamylase produced by *A. niger*, xylanase produced by *A. awamori*, cellulose produced by *Trichoderma reesii*, pectinases and proteases produced by *Aspergillus* species.

(viii) Heterologous proteins such as bovine chymosin (AAA30449) and glucoamylase (JC6538) produced by *A. niger*, the human cytokine interleukin 6 (M18403) produced mainly by *A. niger* and *A. sojae*, manganese peroxidase (AAB30859) produced by *A. niger*, human interferon alpha (NM_024013) and corticosteroid binding globulin (A28321) produced by *A. nidulans*, and human lactoferrin (AAW71443) produced by *A. niger* or *Fusarium venenatum*.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, New York (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Strains: *C. gloeosporioides* f. sp. *aeschynomene* strain 3.1.3 was used. Transgenic strains were produced by electroporation of germinated spores as described by Robinson and Sharon (1999). All experiments were conducted with the wild type isolate and with the transgenic isolates Bcl-15 and Bcl-21.

Media and growth conditions: The following agar (solid) and liquid media (Robinson and Sharon, 1999, Robinson et al., 1998) were used (all are per 1 liter): Emerson's (EMS) medium-4 g yeast extract, 2 g soluble starch, 2.5 g $Na_2HPO_4$, 0.5 g $MgSO_4 7H_2O$; Regeneration (REG) medium-145.7 mannitol, 4 g yeast extract, 1 g soluble starch; Pea Juice medium-900 g frozen peas added to 1.6 liter water and cooked for 15 min. The liquid phase was filtered, brought to 2 liters volume and autoclaved. Solid media (EMS and REG) contained 16 g agar/liter. Liquid cultures were agitated at 190 rpm. Cultures were grown in continuous fluorescent light at 28° C., except when the effect of temperature was examined. For Oxygen stress experiments, $H_2O_2$ (Merck, 003932-7) was added to warm REG agar medium and 10 ml were added to 50 mm Petri dishes. The medium was allowed to solidify and used immediately.

Figure 7:
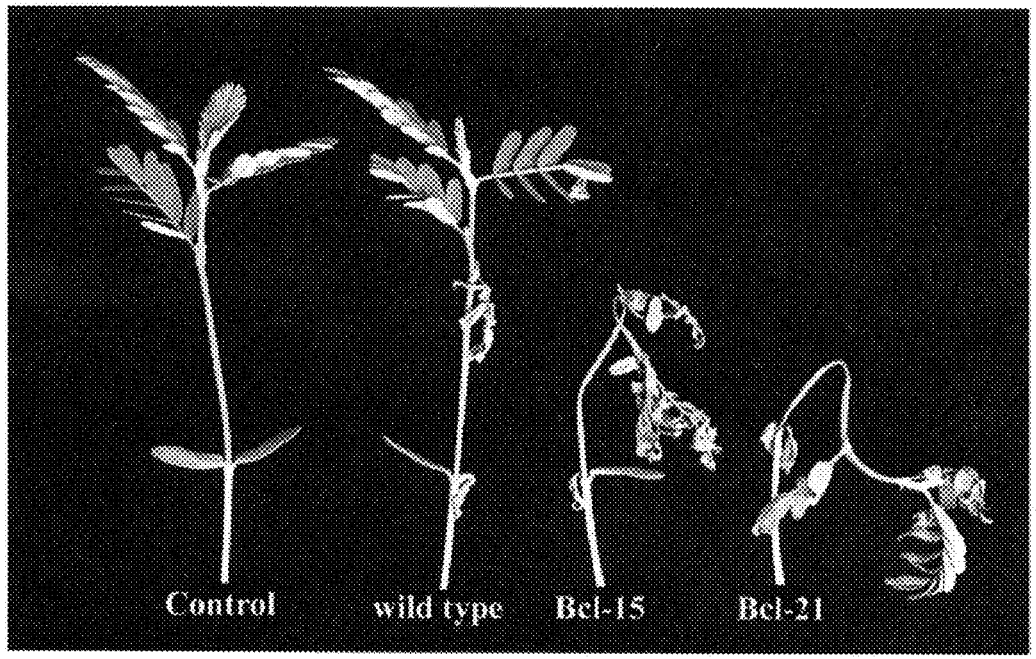
Figure 8A:
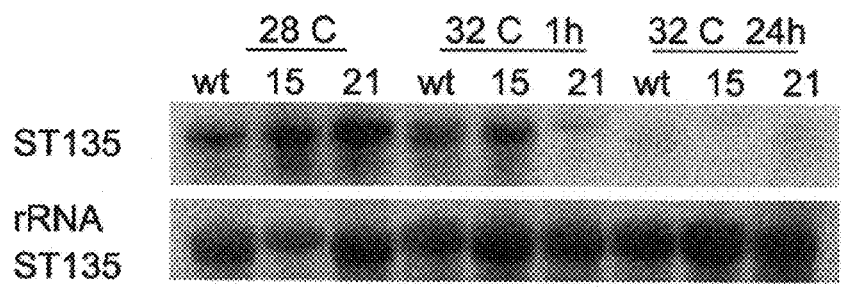
Figure 8B:
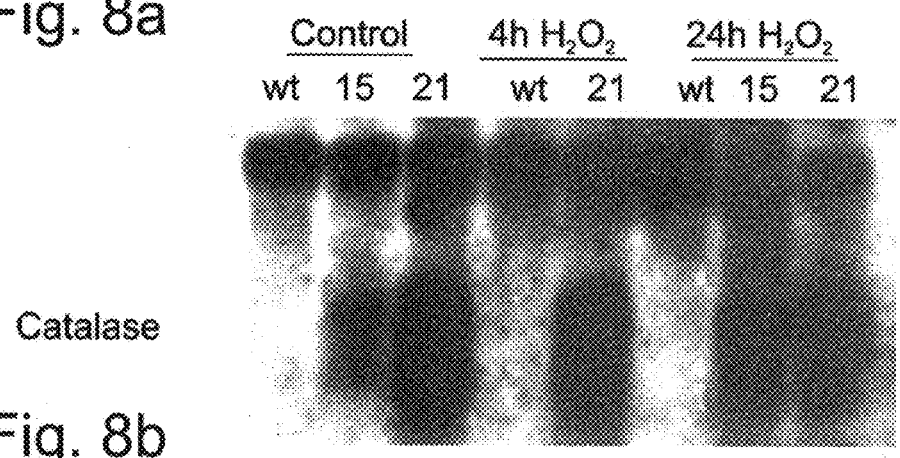
Figure 8C:
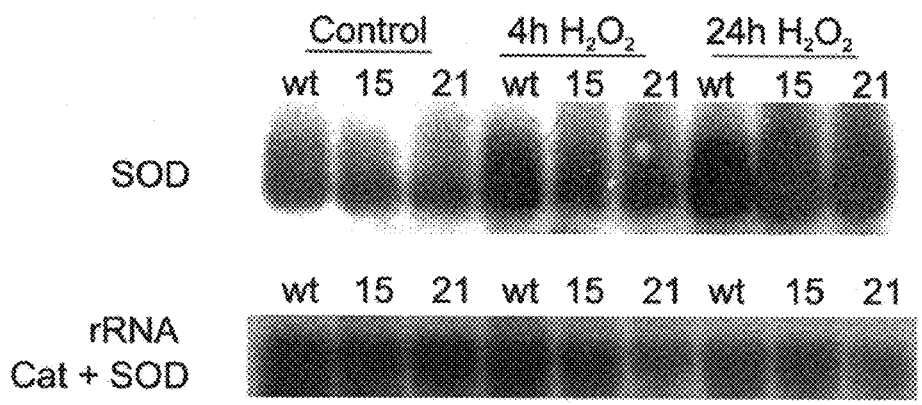
Figure 9:
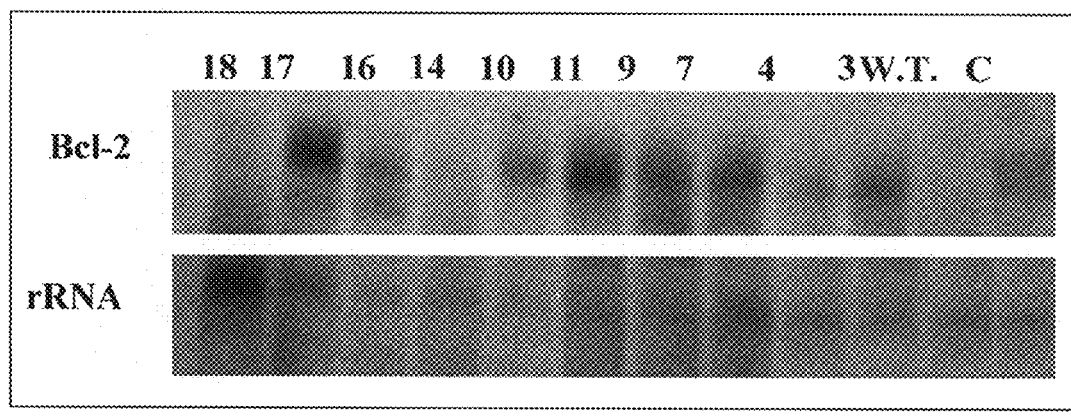
Figure 10:
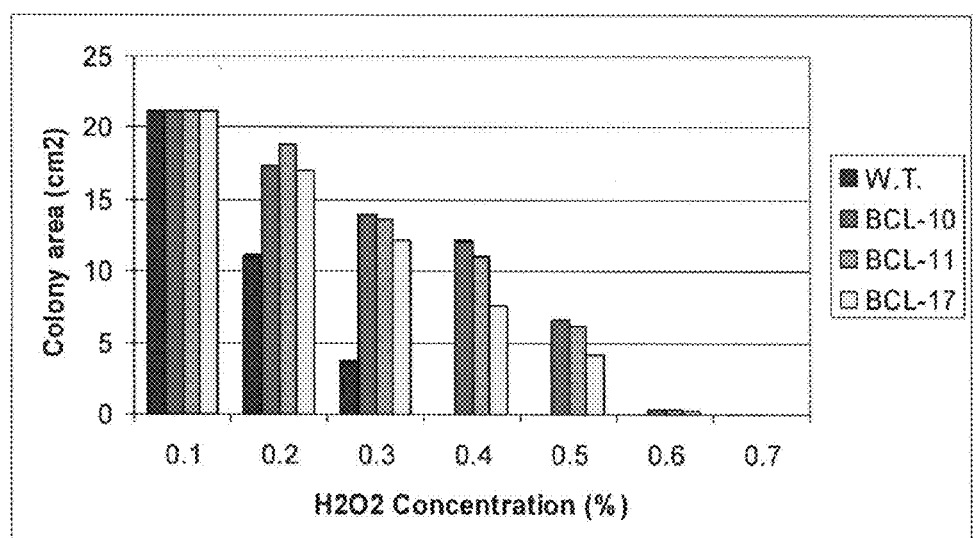
Figure 11:
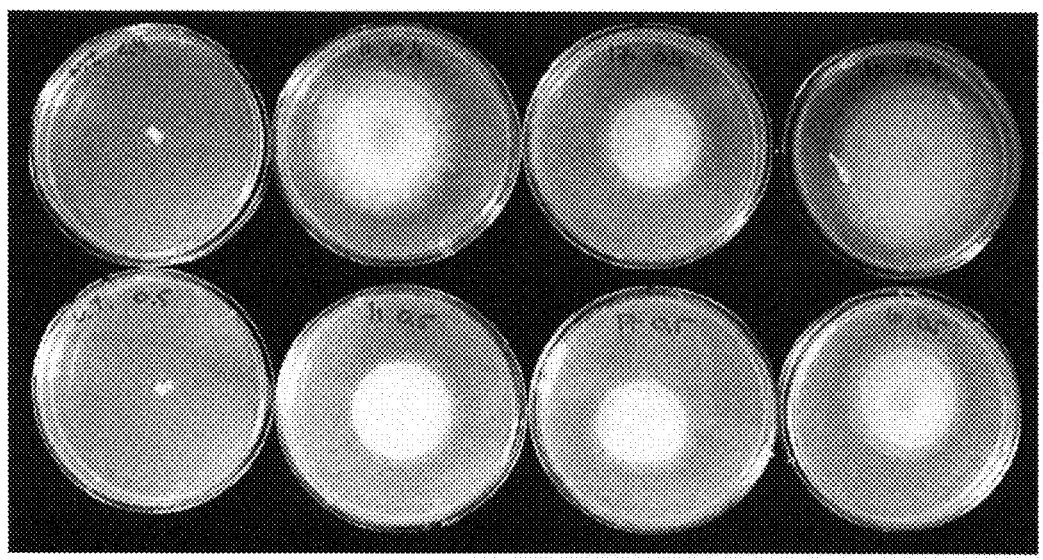

DNA procedures: Bcl-2 expression vector was constructed by cloning the human Bcl-2 gene (GenBank Accession No. M13995) under control of the *Aspergillus nidulans* gpdh promoter (Punt et al., 1987, Gene, 56: 117-124). The Bcl-2 ORF was amplified by PCR using the primers:

GCATAGATCTTTCACTTGTGGCCC (SEQ ID NO:1) and GGAACCATGGCGCACGCTGGGAGAACGGGC (SEQ ID NO:2). The PCR product was cloned into the pUC57-T PCR cloning vector (MBI-Fermentas, #SD0171), the Bcl-2 fragment was excised using Nco I and Bgl II restriction enzymes and ligated into pKSh52-1 in frame with the gpdh promoter to yield the final pSBCl-2 expression vector. DNA extraction and hybridizations were conducted according to published protocols (Robinson and Sharon, 1999, Curr Genet 36:98-104; Molecular Cloning: A laboratory Manual" Sambrook et al., (1989)). Briefly, fungi were grown for 48 h in Pea Juice medium, mycelium were harvested, dried overnight under vacuum and then ground in liquid nitrogen. DNA was extracted using extraction buffer as described (Robinson and Sharon, 1999). Southern blot analysis was performed with 10 μg DNA according to published protocols (Sambrook et al., 1989) using a hybond N+ nylon membrane (Amersham Biosciences, #RPN203B).

Effect of Bcl-2 expression on spore production, stress resistance and survival: The effect of Bcl-2 expression on spore production was tested on solid media using 90 mm Petri dishes with 20 ml agar medium. To test the effect of temperature on vegetative growth, a mycelial plug was placed in the middle of a 50 mm Petri dish and colony area was calculated after 5 days. The effect of UV on survival of conidia was determined by exposing $1\times10^7$ conidia to UV irradiation (254 nm, 12.5 kJ/$cm^2$) supplied by a UV cross linker (Hoefer, Germany). Conidia were then diluted and plated on REG agar medium. The number of colonies was scored after 2 days and survival rates were calculated by dividing the number of colonies developing after treatment by the number of colonies developing from untreated, control conidia. The effect of $H_2O_2$ on fungal growth was tested by growing the fungus on solid REG medium with increasing concentrations of $H_2O_2$. A plug of mycelium was placed in the middle of the plate. The plates were placed in a light protected box and incubated for 5 days at 28° C. after which colony area was determined. All experiments were conducted in triplicate and standard error was calculated using the Microsoft Excel statistical package. Experiments were repeated at least twice. Liquid culture experiments were conducted in 50 ml polystyrene tubes (Miniplast, Ein Shemer, Israel) with 10 ml medium inoculated with $1\times10^7$ conidia. Each time point represents samples from three tubes.

Pathogenicity: Conidia suspensions of the wild type and Bcl-2 isolates were prepared as described (Barhoom and Sharon, Fung. Genet. Biol. 2004, 41: 317-326). In each treatment six *Aeschynomene virginica* plants were inoculated with a water suspension containing $5\times10^4$ or $5\times10^3$ conidia per ml of the wild type or the Bcl-2 isolates. Pure water was used as control. After inoculation the plants were incubated at 100% RH for the first 24 h and then left uncovered for the rest of the experiment. After 6 days the plants were photographed and fresh weight recorded (FIG. 7, Table 2). Each experiment included 6 plants per treatment and was repeated three times with similar results.

Experimental Results

Example I

Figure 1B:
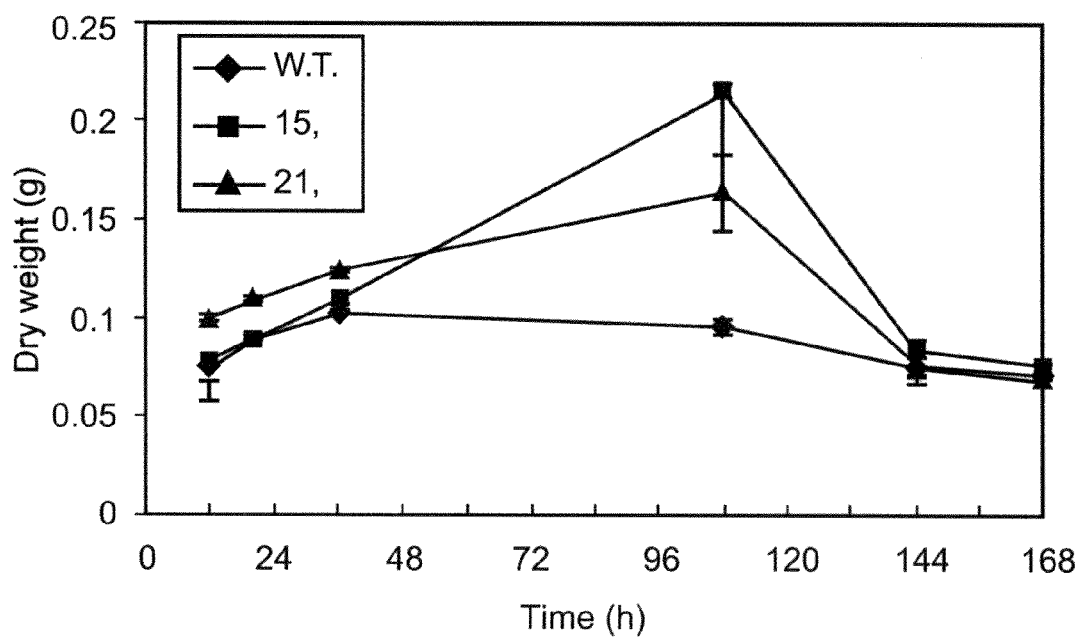
Figure 2A:
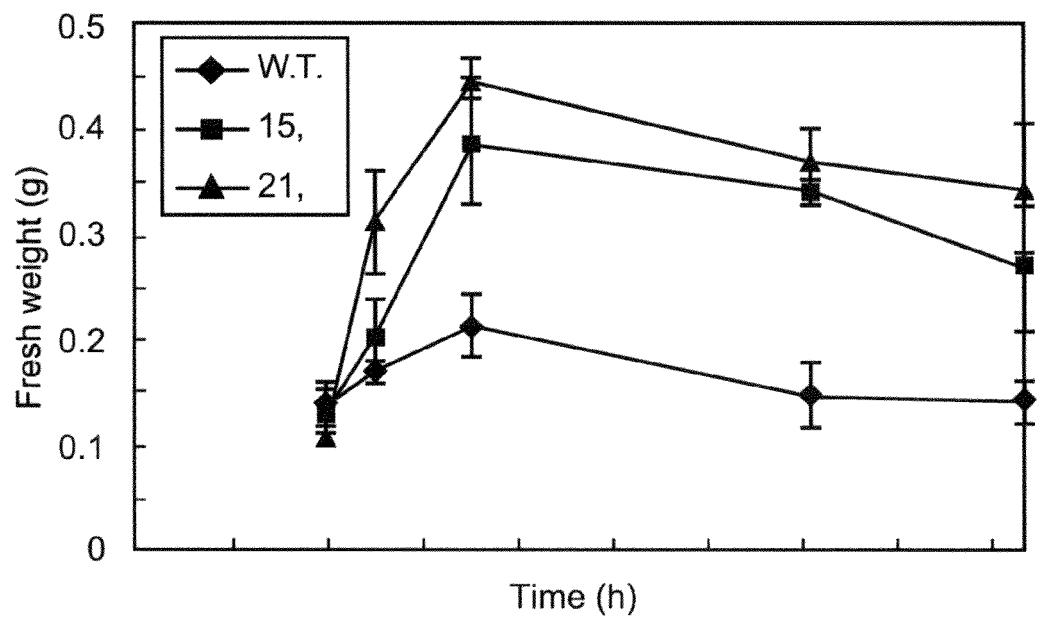
Figure 2B:
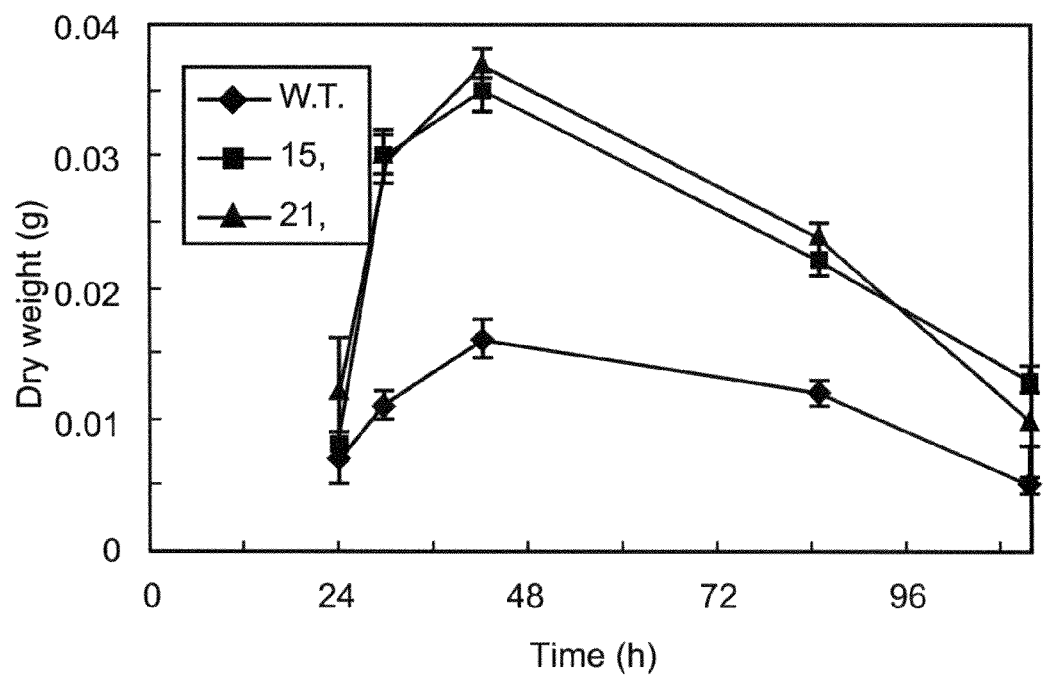
Figure 3A:
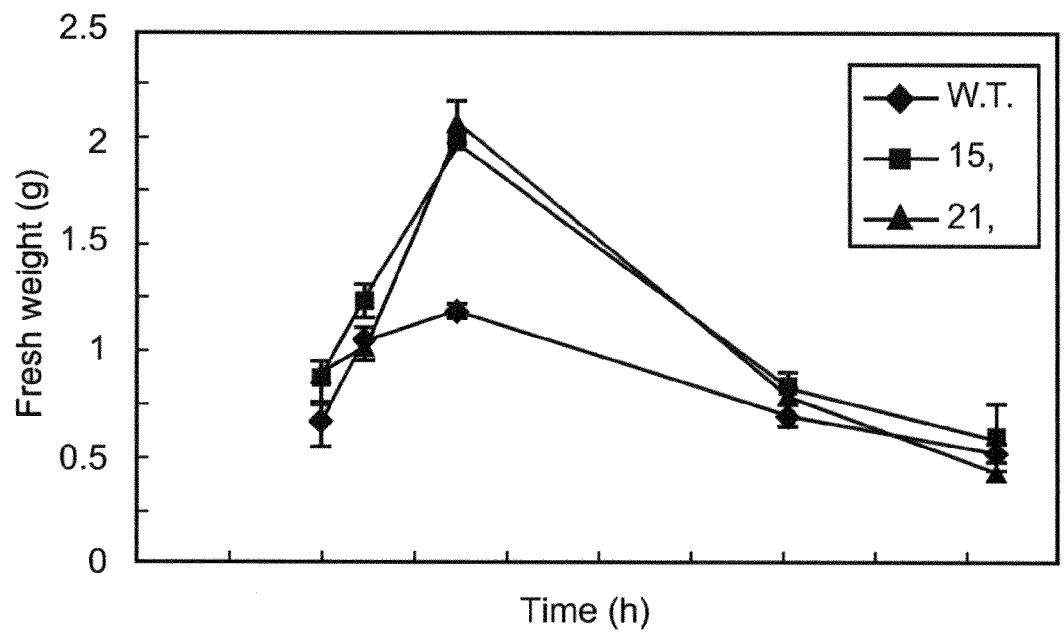
Figure 3B:
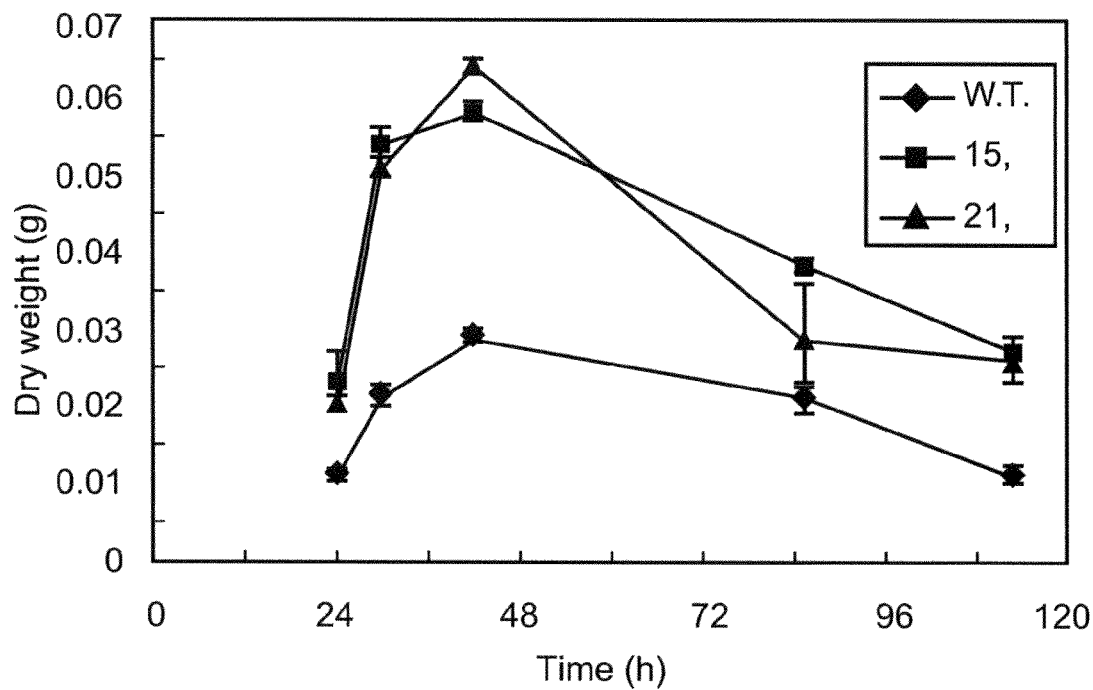

Bcl-2 expression enhances growth rate and biomass production in liquid culture. To test the effect of expression of the antiapoptosis protein Bcl-2 on growth, the fresh and dry weights of Bcl-2-transgenic isolates were compared with those of wild type during the first 7 days after inoculating 10 ml of media with $1 \times 10^7$ conidia. The transgenic isolates developed more mycelium and continued to accumulate biomass for a significantly longer period of time than the wild type strain in all three media that have been tested (FIGS. 1-3). Differences in growth kinetics were observed in the different media. For example, in REG medium there was no difference between the wild type and the Bcl-2 isolates until 36 hours (FIG. 1). After 36 hours the wild type ceased accumulating biomass, while the Bcl-2 isolates continued to accumulate biomass, reaching a maximum at 108 hours, before beginning to decline. At 144 hours, the biomass of the Bcl-2 cultures, measured as fresh and dry weight, were 2.5 times higher than the biomass of the wild type. Somewhat different kinetics were observed in EMS and Pea Juice media, with the Bcl-2 isolates accumulating significantly more biomass already at 30 hours and reaching a peak at 42 hours (FIGS. 2,3). Greatest fresh and dry biomass development was achieved in pea juice and REG media, respectively. Maximum fresh weight of the Bcl-2 isolates was 2.07 g, at 42 hours (FIG. 3a) compared with 1.18 g fresh weight at 42 hours for wild type isolate (FIG. 3a). Maximum dry weight was 0.215 g at 108 hours (FIG. 1b), compared with 0.103 g dry weight at 36 hours for the wild type isolate (FIG. 1b). In addition, differences in the ratio of dry to fresh weight were observed in the different media, possibly resulting from the type of organs (mycelium versus conidia) preferentially produced under different conditions. For example, in EMS medium there was only slight reduction of fresh weight of the Bcl-2 isolates between 42 and 85 hours, as compared with the significant reduction in dry weight (FIG. 2) at the same time. Thus, expression of the human Bcl-2 gene greatly improves both the rates and maxima of biomass accumulation in the transgenic isolates.

Example II

Bcl-2 expression enhances sporeproduction. To test the effect of expression of human Bcl-2 on spore production, isolates were grown on solid media (either REG or EMS), colony diameter and the number of conidia produced at 4, 5, and 7 days were recorded and the number of conidia per $cm^2$ was calculated. Most significantly, expression of Bcl-2 in the transgenic isolates resulted in early production of large amounts of conidia. When grown in REG, a medium that normally promotes mycelial development, the Bcl-2 isolates achieved nearly 10 times wild type conidia production after 4 or 5 days ($2.4 \times 10^6$ conidia/$cm^2$ at 4 days after inoculation of the colony for Bcl-2 isolates compared to only $2.8 \times 10^5$ conidia/$cm^2$ at 4 and 5 days for wild type isolates), and reached a maximum of $3.5 \times 10^6$ conidia/$cm^2$ after 7 days (FIG. 4). At 7 days post inoculation, conidia production was similar for both wild type and transgenic isolates. When grown in EMS medium, a similar but less striking advantage in conidia production was observed for the Bcl-2 isolates, with the wild type strain achieving maximum spore production at 5 days post inoculation. Thus, when grown on solid media, isolates expressing human Bcl-2 produce between 5 to 10 fold more conidia than the wild type isolate in early growth of the culture.

Example III

Bcl-2 expression enhances culture viability. At room temperature wild type cultures usually cease growing after 7 to 10 days, with colonies dying after about 45 days. To test the effect of Bcl-2 on spore viability we kept Bcl-2 and wild type culture plates at room temperature for two weeks. After two weeks conidia were collected and stained with fluorescein diacetate (FDA), which stains only viable cells. The wild type conidia were clear of cytoplasm, did not stain with FDA, and failed to germinate. In contrast, the Bcl-2 conidia remained fully viable as indicated by the FDA stain, and demonstrated surprisingly high germination rates (data not presented).

When stored at 4° C. on agar plates (REG or EMS medium) growth of the wild type strain is arrested instantly, with the mycelium accumulating melanin and turning black within two weeks. The colony remains viable for as long as one year afterward. Unexpectedly, when 5 to 7 day old Bcl-2 colonies were transferred to storage at 4° C. they continued to grow at a slow rate, produced abundant conidia and retained the orange color characteristic of juvenile cultures for the duration of the experiment (18 months) (FIG. 5). It is expected that the transgenic isolates would have maintained growth, conidia production and the orange color through even greater periods of cold storage. Thus, Bcl-2 expression confers greatly enhanced viability to cultures grown on solid media at room temperature and in cold. Together with the extended viability observed in liquid media (see FIGS. 1-3), these results show that expression of Bcl-2 in the transgenic isolates prevents natural senescence and death processes, resulting in phenotypes of surprising robustness and extended longevity.

Example IV

Bcl-2 expression enhances stress resistance: effects of UV, oxygen stress and temperature. To determine whether expression of human Bcl-2 can delay or prevent activation of processes related to senescence and death by environmental conditions, we tested the effects of extremes of UV, $H_2O_2$ and temperature on conidia survival. When exposed to UV irradiation sufficient to induce 99% conidia mortality in the wild type strain (1% survival) (254 nm, 12.5 $kJ/cm^2$), the Bcl-2 isolates #15 and #21 retained 3.91%±0.88 and 4.75%±0.77 survival rates, respectively. Thus, expression of Bcl-2 likely protects against UV-induced DNA derangement.

Oxygen stress was tested by exposing the fungi to peroxide ($H_2O_2$). When exposed to $H_2O_2$ concentrations sufficient to cause over 60% inhibition of mycelial growth in the wild type strain (0.05% v/v $H_2O_2$), the Bcl-2 isolates #15 and #21 retained normal growth rate and were affected to similar levels only at 0.1 to 0.2% v/v $H_2O_2$ $_{(Table}$ 2). Thus, expression of Bcl-2 protects against $H_2O_2$ oxygen stress, and most likely also against other sources of oxidative stress.

TABLE 2

| Enhanced resistance to $H_2O_2$ by Bcl-2 transgenic isolates | | | |
|---|---|---|---|
| Concentration of | Area of colony after 5 days ($cm^2$) | | |
| $H_2O_2$(%) | W.T. | Bcl-2 #15 | Bcl-2 #21 |
| 0.035 | 8.35 ± 0.05 | 9.07 ± 0.03 | 9.96 ± 0.06 |
| 0.05 | 3.57 ± 0.07 | 8.03 ± 0.02 | 7.67 ± 0.09 |
| 0.1 | 2.83 ± 0.07 | 4.62 ± 0.06 | 3.25 ± 0.05 |
| 0.2 | 2.07 ± 0.05 | 2.44 ± 0.20 | 3.14 ± 0.06 |

Figure 6:
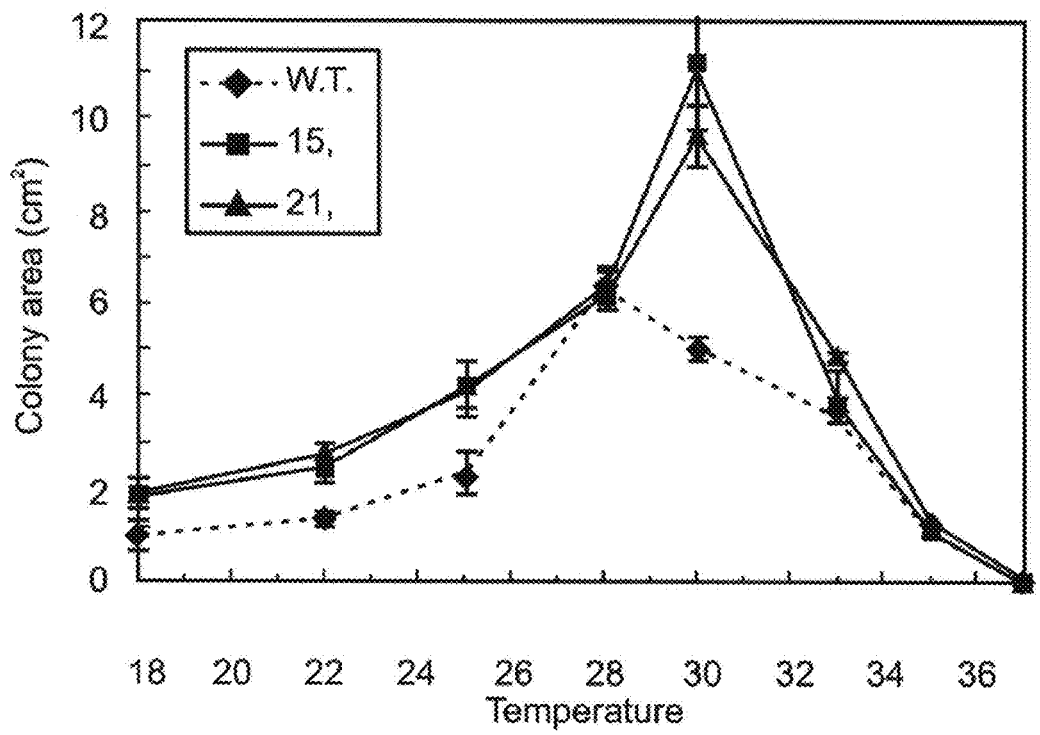

The Bcl-2 isolates were also less sensitive to temperature stress. At the optimal temperature of 28° C., the Bcl-2 and wild type strains exhibited similar growth rates. However, at supra-optimal (28°-36° C.) temperatures, the Bcl-2 isolates had significantly higher growth rate than the wild type strain (FIG. 6). Neither the wild type nor the Bcl-2 strains survived at 37° C. Similarly, at sub-optimal temperatures (<28° C.) the Bcl-2 isolates demonstrated a higher growth rate at all temperatures tested. Thus, although expression of human Bcl-2 is not sufficient to protect from acute stresses such as high temperatures, Bcl-2 expression confers longevity and remarkable resistance to stress conditions to the transgenic isolates.

Example V

Pathogenicity

The pathogenicity of *C. gloeosporioides* wild type and Bcl-2 isolates #15 and #21 was examined using *A. virginica* plants. Table 3 below and FIG. 7 summarize the results.

TABLE 3

Fresh weight of plants infected with $5 \times 10^3$ conidia/ml of wild type and Bcl-2-transgenic *C. gloeosporioides* 6 days post inoculation

| [a]Treatment | Fresh weight (mg) |
|---|---|
| Wild type | 217 ± 10 |
| Bcl2 #15 | 120 ± 10 |
| Bcl2 #21 | 128 ± 6 |
| Control | 590 ± 20 |

[a]Plants were inoculated with $5 \times 10^3$ conidia/ml

As is demonstrated by the results provided in Table 3 and illustrated in FIG. 7, expression of Bcl-2 in *C. gloeosporioides* drastically effected fungal virulence. Bcl-2 transgenic isolates #15 and #21 killed plants with fewer spores and much faster than the wild type isolate. At least $5\times10^4$ conidia/ml of the wild type isolate are necessary to efficiently kill plants within 6 days; 1/10 this amount ($5\times10^3$ conidia/ml) of the Bcl-2 transgenic isolates was sufficient to efficiently kill plants within 2-3 days. These changes in virulence did not cause a change in host range as determined by infectivity assay of the transgenic isolates on corn and several other plant species that normally do not serve as host for *C. gloeosporioides.*

Since Bcl-2 expression in pathogenic fungi induces such a dramatic change in the ability of such fungi to infect and kill plants, such transformation can be utilized to generate enhanced weed control agents which will be effective at lower spore titers and over a decreased period of incubation.

Example VI

Bcl-2 Induces Stress Related Genes

Heat stress: Northern blot analysis of the Bcl-2 isolates described above revealed elevated transcription levels of several stress related genes. The wild type and Bcl-2 isolates #15 and #21 were grown at 28° C. (optimal temperature) and at 32° C. (supra-optimal temperature) for one hour or overnight. Total RNA was extracted and probed with a *C. gloeosporioides* homologue of the STI35 gene (SEQ ID NO:3) which is a known stress response gene that is induced by several stress signals including heat (J. Bacteriol 1990, 172:4522-8). At 28° C., transcript level of the STI35 was 2.5 -3 times higher in the Bcl-2 isolates as compared to the wild type isolate (FIG. 8A). Following one hour at 32° C., the transcript level of the wild type fungus reached levels similar to that of the Bcl-2 isolates, while following an incubation of 24 h at 32° C. the transcript level was reduced in all isolates.

Oxidative stress: Isolates were grown in regular media or in media containing 0.04% oxygen peroxide ($H_2O_2$) for 4 h or for 24 h. Total RNA was extracted and membranes were probed with *C. gloeosporioides* homologues of catalase (SEQ ID NO:4) and super oxide dismutase (SOD) (SEQ ID NO:5) encoding genes (FEMS Microbiol Lett 2001, 202: 103-7; Fung Genet Biol 2002, 36:155-65, respectively). The catalase probe reacted with a 2 kb transcript that had a constant level in all isolates at all treatments, but in the Bcl-2 isolates it also reacted with another transcript of lower molecular weight that was not detected in the wild type isolate (FIG. 8B). Different catalase species that react in a different way to oxidative stress are known in other organisms (Bussink and Oliver, 2001, Eur J Biochem 268: 15-24). Expression levels of the SOD gene were elevated following 4 h of incubation in the presence of $H_2O_2$; increase in expression levels was also observed in the wild type isolate following a 24 h incubation in the presence of $H_2O_2$, while it was already elevated in the Bcl-2 isolates at 4 h, and further enhanced after 24 h in $H_2O_2$ (FIG. 8C).

These results support the findings described above which show elevated resistance of the Bcl-2 isolates to various stresses. They also provide a possible explanation for the molecular basis of this phenotype and indicate that Bcl-2 causes a global change in fungal gene activity.

Example VII

*Aspergillus niger* is used extensively in industry for the production of organic acids, particularly citric acid, as well as extracellular enzymes, such as glucoamylase, β-glucanase and pectinase. Moreover, the ability of this filamentous fungus to secrete large amounts of extracellular protein has made it a prime candidate for the development of expression and secretion systems for heterologous proteins of pharmaceutical and industrial interest. In order to examine if the expression of Bcl-2 in other filamentous fungi leads to the phenotypes observed in C.g.a., *Aspergillus niger* transgenic isolates expressing Bcl-2 were produced. The transformation procedure used was according to Yelton et al., 1984 and Unkles et al., 1989 in which, *Aspergillus* protoplasts were prepared and mixed with Bcl-2 expression vector (described above). Hygromycin B resistant colonies were collected and Bcl-2 expression was confirmed by northern blot analysis (FIG. 9).

Isolates 10, 11 and 17 were used for further characterization of the Bcl-2 phenotypes. Since C.g.a. Bcl-2 transgenic isolates were more resistant to oxidative stress, the influence of $H_2O_2$ on mycelium growth was examined also in *A. niger* Bcl-2 transgenic isolates. The transgenic isolates were exposed to different concentrations of $H_2O_2$ and colony area that was developed after 4 days of growth on REG medium was measured. When the wild type and the transgenic isolates were exposed to 0-0.1% v/v $H_2O_2$ maximal growth was observed while 0.7-1% v/v $H_2O_2$ caused to 100% inhibition of mycelia growth (Table 4). However, when both wild type and the transgenic isolates were exposed to $H_2O_2$ concentration sufficient to cause 100% inhibition of mycelia growth in the wild type strain (0.4% v/v $H_2O_2$), the Bcl-2 isolates retained normal growth rate and were affected similarly only at 0.7% v/v $H_2O_2$ (FIGS. 10 and 11).

TABLE 4

Enhanced resistance to $H_2O_2$ by Bcl-2 transgenic isolates

| Concentration of $H_2O_2$ (%) | W.T. | BCL-10 | BCL-11 | BCL-17 | W.T. | BCL-10 | BCL-11 | BCL-17 |
|---|---|---|---|---|---|---|---|---|
| 0 | 21.22 | 21.22 | 21.22 | 21.22 | 0 | 0 | 0 | 0 |
| 0.01 | 21.22 | 21.22 | 21.22 | 21.22 | 0 | 0 | 0 | 0 |
| 0.04 | 21.22 | 21.22 | 21.22 | 21.22 | 0 | 0 | 0 | 0 |
| 0.08 | 21.22 | 21.22 | 21.22 | 21.22 | 0 | 0 | 0 | 0 |
| 0.1 | 21.22 | 21.22 | 21.22 | 21.22 | 0 | 0 | 0 | 0 |
| 0.2 | 11.09 | 17.34 | 18.84 | 17.04 | 0.05 | 0.007 | 0.007 | 0.03 |
| 0.3 | 3.66 | 14 | 13.58 | 12.12 | 0.01 | 0.017 | 0.009 | 0.05 |
| 0.4 | 0 | 12.12 | 11.09 | 7.69 | 0 | 0.017 | 0.05 | 0.08 |
| 0.5 | 0 | 6.6 | 6.15 | 4.15 | 0 | 0.007 | 0.007 | 0.007 |
| 0.6 | 0 | 0.31 | 0.34 | 0.22 | 0 | 0.017 | 0.017 | 0.017 |
| 0.7 | 0 | 0 | 0 | 0 | 0 | 0 | 0 | 0 |
| 0.8 | 0 | 0 | 0 | 0 | 0 | 0 | 0 | 0 |
| 0.9 | 0 | 0 | 0 | 0 | 0 | 0 | 0 | 0 |
| 1 | 0 | 0 | 0 | 0 | 0 | 0 | 0 | 0 |

These results which are similar to the results observed in C.g.a. indicate that the human Bcl-2 expression protects also *Aspergillus niger* transgenic isolates against oxidative stress.

Figure 12A:
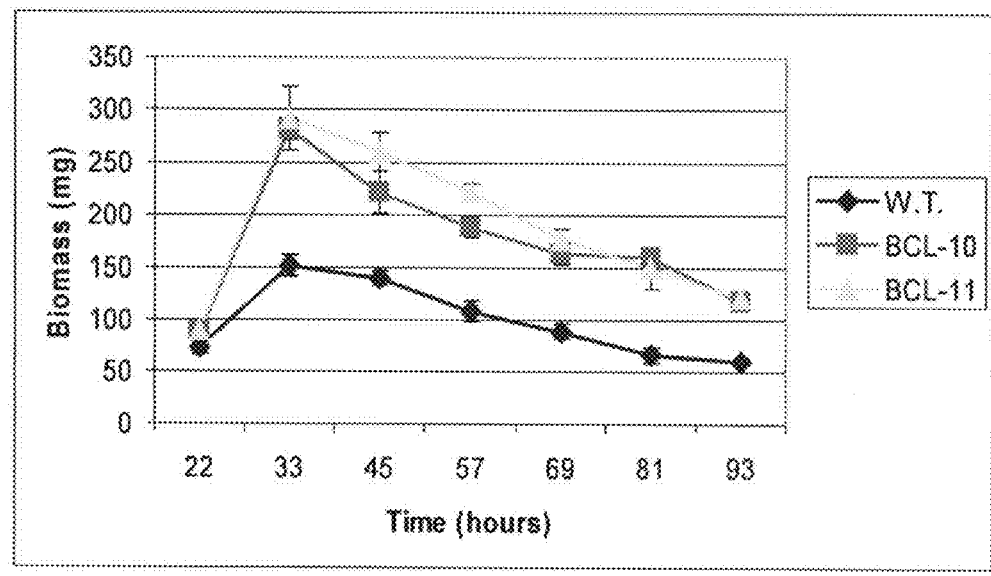
Figure 12B:
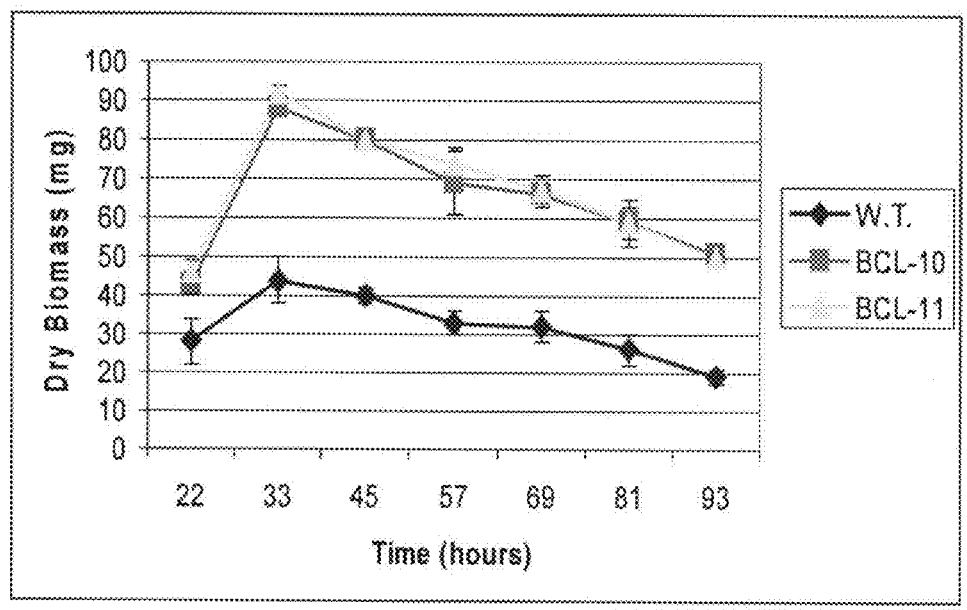

In addition, Bcl-2 expression enhances biomass production of *Aspergillus niger* transgenic isolates grown in liquid culture in a manner similar to that observed for C.g.a. Fresh and dry weights of Bcl-2 transgenic isolates were compared with those of wild type during the first four days after inoculating 10 ml of REG medium with $1 \times 10^6$ conidia. The transgenic isolates developed more mycelium than the wild type strain (FIGS. 12A-B). At 33 hours, when both the wild type and the transgenic isolates reached a maximum biomass and before beginning to decline, the maximum dry weight measured in the Bcl-2 isolates was 92 mg compared to 44 mg in the wild type. The higher rates of biomass accumulation of the Bcl-2 isolates were observed not just at specific time point but during all the experiment.

These results indicate that the expression of the human Bcl-2 gene greatly improves both the rates and maxima of biomass accumulation in the *A. niger* transgenic isolates.

Both experiments biomass production and resistance to oxidative stress were conducted twice and included 3 replications per each time point or per each $H_2O_2$ concentration respectively per each isolate. Moreover, these experiments were conducted according the procedures used in the characterization of C.g.a. Bcl-2 transgenic isolates which are optimal to C.g.a. but not to *A. niger*. The use in *A. niger* favorable conditions might improve these phenotypes even more than the observed results.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and GenBank accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A filamentous fungus belonging to a species selected from the group consisting of *Colletotrichum gloeosporioides* and *Aspergillus niger*, said fungus comprising an exogenous polynucleotide capable of expressing a full-length Bcl-2 polypeptide, wherein said exogenous polynucleotide comprises a promoter sequence operably linked to a nucleic acid sequence encoding said full-length Bcl-2 polypeptide, the filamentous fungus exhibiting accelerated growth as compared to a wild type filamentous fungus.

2. The filamentous fungus of claim 1, wherein said promoter sequence is an *Aspergillus nidulans* gpdh promoter and said nucleic acid sequence is human Bcl-2.

3. The filamentous fungus of claim 1, wherein the filamentous fungus exhibits accelerated conidia accumulation as compared to said wild type filamentous fungus when grown in solid medium.

4. The filamentous fungus of claim 1, wherein the filamentous fungus exhibits extended biomass accumulation as compared to said wild type filamentous fungus when grown in liquid medium.

5. The filamentous fungus of claim 1, wherein the filamentous fungus remains viable in storage for a time period longer than said wild type filamentous fungus when grown on solid media.

6. The filamentous fungus of claim 1, wherein the filamentous fungus exhibits increased resistance to a stress selected from the group consisting of temperature, oxidative and radiation stress, as compared to said wild type filamentous fungus.

7. The filamentous fungus of claim 6, wherein said oxidative stress is exposure to oxygen radical concentration equal to at least 0.05% (v/v) $H_2O_2$ concentration, and whereas said increased resistance is at least 100% greater colony area as compared to said wild type filamentous fungus.

8. A method of enhancing growth of a filamentous fungus, the method comprising expressing within the filamentous fungus an exogenous polynucleotide encoding a full-length Bcl-2 polypeptide, wherein said exogenous polynucleotide comprises a promoter sequence operably linked to a nucleic acid sequence encoding said full-length Bcl-2 polypeptide, said filamentous fungus belonging to a species selected from the group consisting of *Colletotrichum gloeosporioides* and *Aspergillus niger*, thereby enhancing growth of the filamentous fungus.

9. The method of claim 8, wherein enhancing growth is effected by a method selected from the group consisting of accelerating conidia accumulation and extending biomass accumulation.

10. The method of claim 8, wherein the growth is determined by measuring colony area.

11. The method of claim 8, wherein said promoter sequence is an *Aspergillus nidulans* gpdh promoter and said nucleic acid sequence is human Bcl-2.

12. The filamentous fungus of claim 1, being capable of accumulating between 2 to 2.5 times more fungal biomass per culture compared to wild type fungus.

* * * * *